United States Patent
Aman et al.

(10) Patent No.: US 9,109,036 B2
(45) Date of Patent: Aug. 18, 2015

(54) IMMUNOGENIC COMPOSITION COMPRISING ALPHA-HEMOLYSIN OLIGOPEPTIDES

(75) Inventors: Mohammad Javad Aman, Rockville, MD (US); Rajan Prasad Adhikari, Gaithersburg, MD (US); Hatice Karauzum, Silver Spring, MD (US); Kelly Lyn Warfield, Adamstown, MD (US); Tam Luong Nguyen, Gaithersburg, MD (US)

(73) Assignee: Integrated BioTherapeutics, Inc., Gaithersburg, MD (US)

(*) Notice: Subject to any disclaimer, the term of this patent is extended or adjusted under 35 U.S.C. 154(b) by 0 days.

(21) Appl. No.: 13/984,226

(22) PCT Filed: Feb. 6, 2012

(86) PCT No.: PCT/US2012/024031
§ 371 (c)(1),
(2), (4) Date: Nov. 21, 2013

(87) PCT Pub. No.: WO2012/109167
PCT Pub. Date: Aug. 16, 2012

(65) Prior Publication Data
US 2014/0079709 A1   Mar. 20, 2014

Related U.S. Application Data

(60) Provisional application No. 61/440,757, filed on Feb. 8, 2011, provisional application No. 61/554,750, filed on Nov. 2, 2011.

(51) Int. Cl.
*A61K 39/085* (2006.01)
*C07K 14/31* (2006.01)
*C07K 16/12* (2006.01)
*A61K 38/00* (2006.01)

(52) U.S. Cl.
CPC ............... *C07K 14/31* (2013.01); *A61K 39/085* (2013.01); *C07K 16/1271* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,027,010 A | 5/1977 | Kiselev et al. | |
| 4,327,082 A | 4/1982 | Armitage | |
| 7,754,225 B2 | 7/2010 | Fattom et al. | |
| 2008/0131457 A1 | 6/2008 | Taylor et al. | |
| 2011/0027265 A1 | 2/2011 | Bubeck-Wardenburg et al. | |

FOREIGN PATENT DOCUMENTS

| | | |
|---|---|---|
| WO | 2007/143451 A2 | 12/2007 |
| WO | WO 2009/029831 A1 | 3/2009 |
| WO | WO 2010/081875 A1 | 7/2010 |
| WO | WO 2010/119343 A2 | 10/2010 |
| WO | 2011/051917 A1 | 5/2011 |
| WO | 2013/030378 A1 | 3/2013 |
| WO | 2013/092985 A1 | 6/2013 |

OTHER PUBLICATIONS

Cruse et al., Illustrated Dict. of Immunology, 2nd ed., CRC Press, 2003, p. 46,166,382.*
Bowie et al. (Science, 1990, 247:1306-1310).*
Greenspan et al. (Nature Biotechnology 7: 936-937, 1999).*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
Appelbaum, P. C., "The emergence of vancomycin-intermediate and vancomycin-resistant *Staphylococcus aureus*," *Clin. Microbiol. Infect.* 12S(1):16-23, Blackwell Science, France (2006).
Bramley, A. J. et al., "Roles of alpha-toxin and beta-toxin in virulence of *Staphylococcus aureus* for the mouse mammary gland," *Infect. Immun.* 57(8):2489-2494, American Society for Microbiology, United States (1989).
Bubeck-Wardenburg, J., et al., "Surface proteins and exotoxins are required for the pathogenesis of *Staphylococcus aureus* pneumonia," *Infect. Immun.* 75(2):1040-1044, American Society for Microbiology, United States (2007).
Bubeck-Wardenburg, "Vaccine protection against *Staphylococcus aureus* pneumonia," J. Exp. Med. 205(2):287-294, Rockefeller University Press, United States (2008).
Chambers, H. F., "Methicillin-resistant staphylococci," *Clin. Microbiol. Rev.* 1(2):173-186, American Society for Microbiology, United States (1988).
Cunnion, K. M., et al., "Capsule production and growth phase influence binding of complement to *Staphylococcus aureus*," *Infect. Immun.* 69(11):6796-6803, American Society for Microbiology, United States (2001).
Enkhbaatar, P., et al., "Novel ovine model of methicillin-resistant *Staphylococcus aureus*-induced pneumonia and sepsis," *Shock* 29(5):642-649, BioMedical Press, United States (2008).
Fattom, A. I., et al., "Laboratory and clinical evaluation of conjugate vaccines composed of *Staphylococcus aureus* type 5 and type 8 capsular polysaccharides bound to *Pseudomonas aeruginosa* recombinant exoprotein A," Infect. Immun. 61(3):1023-1032, American Society for Microbiology, United States (1993).
Fattom, A. I., et al., "A *Staphylococcus aureus* capsular polysaccharide (CP) vaccine and CP-specific antibodies protect mice against bacterial challenge," *Infect. Immun.* 64(5):1659-1665, American Society for Microbiology, United States (1996).
Fattom, A. I., et al., "Development of StaphVAX, a polysaccharide conjugate vaccine against *S. aureus* infection: from the lab bench to phase III clinical trials," *Vaccine* 22:880-887, Elsevier Science, Netherlands (2004).

(Continued)

*Primary Examiner* — Brian J Gangle
(74) *Attorney, Agent, or Firm* — Thompson Coburn LLP

(57) ABSTRACT

The present invention provides immunogenic compositions useful in prevention and treatment of *Staphylococcus aureus* infection. In particular, the present invention provides methods of inducing an immune response against an alpha-hemolysin-expressing *S. aureus*, methods of preventing or treating *S. aureus* infections, and composition for preventing or treating *S. aureus* infections.

18 Claims, 13 Drawing Sheets

(56) References Cited

OTHER PUBLICATIONS

Fournier, J-M., et al., "Purification and characterization of *Staphylococcus aureus* type 8 capsular polysaccharide," Infect. Immun. 45(1):87-93, American Society for Microbiology, United States (1984).
Fournier, J-M., et al., "Isolation of type 5 capsular polysaccharide from *Staphylococcus aureus*," Ann. Inst. Pasteur Microbiol. 138:561-567, Elsevier, France (1987).
Hidron, A. I., et al., "Emergence of community-acquired meticillin-resistant *Staphylococcus aureus* strain USA300 as a cause of necrotising community-onset pneumonia," *Lancet Infect. Dis.* 9:384-392, Elsevier Science, United States (2009).
Kennedy, A. D., et al., "Targeting of alpha-hemolysin by active or passive immunization decreases severity of USA300 skin infection in a mouse model," *J. Infect. Dis.* 202(7):1050-1058, American Society for Microbiology, United States (2010).
Kephart, P. A., et al., "Comparison of the investigational drug, LY146032, with vancomycin in experimental pneumonia due to methicillin-resistant *Staphylococcus aureus*," *J Antimicrob Chemother.* 21:33-39, Oxford University Press, England (1988).
Kuehnert, M. J., et al., "Methicillin-resistant-*Staphylococcus aureus* hospitalizations, United States" *Emerg. Infect. Dis.* 11(6): 868-872, National Center for Infectious Diseases, Centers for Disease Control and Prevention, United States (2005).
Lee, J. C., et al., "Protective efficacy of antibodies to the *Staphylococcus aureus* type 5 capsular polysaccharide in a modified model of endocarditis in rats," *Infect. Immun.* 65(10):4146-4151, American Society for Microbiology, United States (1997).
Maira-Litrán, T., et al., "Comparative opsonic and protective activities of *Staphylococcus aureus* conjugate vaccines containing native or deacetylated Staphylococcal Poly-N-acetyl-beta-(1-6)-glucosamine," *Infect Immun.* 73(10):6752-6762, American Society for Microbiology, United States (2005).
McElroy, M. C., et al., "Alpha-toxin damages the air-blood barrier of the lung in a rat model of *Staphylococcus aureus*-induced pneumonia," *Infect Immun.* 67(10):5541-5544, American Society for Microbiology, United States (1999).
McKenney, D., et al., "Broadly protective vaccine for *Staphylococcus aureus* based on an in vivo-expressed antigen," *Science* 284:1523-1527, American Association for the Advancement of Science, United States (1999).
McKenney, D., et al., "Vaccine potential of poly-1-6 beta-D-N-succinylglucosamine, an immunoprotective surface polysaccharide of *Staphylococcus aureus* and *Staphylococcus epidermidis*," J. Biotechnol. 83:37-44, Elsevier Science B.V., Netherlands (2000).
Menzies, B. E., et al., "Passive immunization with antiserum to a nontoxic alpha-toxin mutant from *Staphylococcus aureus* is protective in a murine model," *Infect. Immun.* 64(5): 1839-1841, American Society for Microbiology, United States (1996).
Moreau, M., et al., "Structure of the type 5 capsular polysaccharide of *Staphylococcus aureus*," *Carbohydr. Res.* 201:285-297, Elsevier Science Publishers B.V., Netherlands (1990).
Mulligan, M. E., et al., "Methicillin-resistant *Staphylococcus aureus*: a consensus review of the microbiology, pathogenesis, and epidemiology with implications for prevention and management," *Am. J. Med.* 94(3):313-328, The American Journal of Medicine, United States (1993).
Neuhaus, F. C., et al., "A continuum of anionic charge: structures and functions of D-alanyl-teichoic acids in gram-positive bacteria," *Microbiol. Mol. Biol. Rev.* 67(4):686-723, American Society for Microbiology, United States (2003).
O'Riordan, K., et al., "*Staphylococcus aureus* capsular polysaccharides," *Clinical Microbiology Reviews* 17(1):218-234, American Society for Microbiology, United States (2004).
Patel, A. H. et al., "Virulence of protein A-deficient and alpha-toxin-deficient mutants of *Staphylococcus aureus* isolated by allele replacement," *Infect. Immun.* 55(12):3103-3010, American Society for Microbiology, United States (1987).
Poutrel, B., et al., "Type 5 and 8 capsular polysaccharides are expressed by *Staphylococcus aureus* isolates from rabbits, poultry, pigs, and horses," *J. Clin. Microbiol.* 31(2):467-469, American Society for Microbiology, United States (1993).
Ragle, B. E., et al., "Anti-alpha-hemolysin monoclonal antibodies mediate protection against *Staphylococcus aureus* pneumonia," *Infect. Immun.* 77(7):2712-2718, American Society for Microbiology, United States (2009).
Ryding, U., et al., "Antibody response to *Staphylococcus aureus* collagen binding protein in patients with *S. aureus* septicaemia and collagen binding properties of corresponding strains," *J. Med. Microbiol.* 43(5):328-334, Society for General Microbiology, England (1995).
Shinefield, H., et al., "Use of a *Staphylococcus aureus* conjugate vaccine in patients receiving hemodialysis," *N. Engl. J. Med.* 346(7):491-496, Massachusetts Medical Society, United States (2002).
Song, L., et al., "Structure of staphylococcal alpha-hemolysin, a heptameric transmembrane pore," *Science* 274:1859-1866, American Association for the Advancement of Science, United States (1966).
Thakker, M., et al., "*Staphylococcus aureus* Serotype 5 Capsular Polysaccharide Is Antiphagocytic and Enhances Bacterial Virulence in a Murine Bacteremia Model," *Infect. Immun.* 66(11):5183-5189, American Society for Microbiology, United States (1998).
Tollersrud, T., et al., "Genetic and serologic evaluation of capsule production by bovine mammary isolates of *Staphylococcus aureus* and other *Staphylococcus* spp. from Europe and the United States," *J. Clin. Microbiol.* 38(8):2998-3003, American Society for Microbiology, United States (2000).
Tuchscherr, L. P., et al., "Antibodies to capsular polysaccharide and clumping factor A prevent mastitis and the emergence of unencapsulated and small-colony variants of *Staphylococcus aureus* in mice," *Infect. Immun.* 76(12):5738-5744, American Society for Microbiology, United States (2008).
Verghese, A., et al., "LY146032 in a hamster model of *Staphylococcus aureus* pneumonia—effect on in vivo clearance and mortality and in vitro opsonophagocytic killing," *Chemotherapy* 34(6):497-503, Karger, Switzerland (1988).
Wu, T. C., et al., "Chemical characterization of a new surface antigenic polysaccharide from a mutant of *Staphylococcus aureus*," *J. Bacteriol.* 108(2):874-884, American Society for Microbiology, United States (1987).
International Preliminary Report on Patentability for International Application No. PCT/US2012/024031, International Bureau of WIPO, Switzerland, mailed on Aug. 22, 2013.
Database UniProt [Online], "SubName: Full=Alpha-hemolysin domain protein {ECO:0000313|EMBL:EGS89184.1};", XP002734885, retrieved from EBI Accession No. UNIPROT:F9KZ27; Database Accession No. F9KZ27 *sequence*; Oct. 19, 2011.

\* cited by examiner

A

B

IMMUNOGENIC COMPOSITION COMPRISING ALPHA-HEMOLYSIN OLIGOPEPTIDES

CROSS-REFERENCE TO RELATED APPLICATIONS

This application is the National Stage of International Application Number PCT/US2012/024031, filed Feb. 6, 2012, which claims benefit of U.S. Application No. 61/440,757; filed Feb. 8, 2011, and U.S. Application No. 61/554,750; filed Nov. 2, 2011, each of which is incorporated in its entirety by reference herein.

REFERENCE TO SEQUENCE LISTING SUBMITTED ELECTRONICALLY VIA EFS-WEB

The content of the electronically submitted sequence listing (Name: sequencelisting.txt; Size: 7,573 bytes; Date of Creation: Aug. 6, 2013) submitted in this application is incorporated herein by reference in its entirety.

BACKGROUND OF THE INVENTION

Field of Invention

This invention relates to the treatment and prevention of *Staphylococcus aureus* (*S. aureus*) infection. In particular, the invention provides compositions and methods for preventing *S. aureus* infection and treating a disease caused by *S. aureus* infection.

*S. aureus* is a gram positive human pathogen that causes a wide range of infections ranging from minor skin infections such as pimples, impetigo, boils (furuncles), cellulitis folliculitis, carbuncles, scalded skin syndrome, and abscesses, to life-threatening deep infections such as pneumonia, sepsis, endocarditis, meningitis, post-operative wound infections, septicemia, and toxic shock syndrome (Silverstein et al., in Microbiology, Davis et al., eds. (Lippincott, Philadelphia, 1990), pp. 485-506).

Pneumonia is one of the most severe and prominent complications of *S. aureus* infection leading with 50,000 cases per year in the U.S. alone (Kuehnert, et al., *Emerg. Infect. Dis.* 11:868-872, 2005). *S. aureus* pneumonia has been traditionally ventilator associated, but in recent years, it has been recognized also as a major cause of community acquired pneumonia primarily in otherwise healthy children and young individuals.

A significant increase in *S. aureus* isolates that exhibit resistance to most of the antibiotics currently available to treat infections has been observed in hospitals throughout the world. The development of penicillin to combat *S. aureus* was a major advance in infection control and treatment. Unfortunately, penicillin-resistant organisms quickly emerged and the need for new antibiotics was paramount. With the introduction of every new antibiotic, *S. aureus* has been able to counter with β-lactamases, altered penicillin-binding proteins, and mutated cell membrane proteins allowing the bacterium to persist. Moreover, methicillin-resistant *S. aureus* (MRSA) and multidrug resistant organisms have emerged and established major footholds in hospitals and nursing homes around the world. (Chambers, H. F., *Clin Microbiol Rev.*, 1:173, 1988; and Mulligan, M. E., et al., *Am J Med.*, 94:313, 1993). Today, almost half of the Staphylococcal strains causing nosocomial infections are resistant to all antibiotics except vancomycin and linezolid. Since many vancomycin intermediate resistant *S. aureus* (VISA) among MRSA, and a few vancomycin resistant *S. aureus*, have been reported in the literature it appears to be only a matter of time before vancomycin will become ineffective as well. (Appelbaum P C., *Clin Microbiol Infect.*, 12 Suppl 1:16-23, 2006).

Natural immunity to *S. aureus* infections remains poorly understood. Typically, healthy humans and animals exhibit a high degree of innate resistance to *S. aureus* infections. Protection is attributed to intact epithelial and mucosal barriers and normal cellular and humoral responses. Titers of antibodies to *S. aureus* components are elevated after severe infections (Ryding et al., *J Med Microbiol*, 43(5):328-334, 1995). However, to date, there is no serological evidence of a correlation between these acquired antibody titers and human immunity.

The virulence of *S. aureus* is due to a combination of numerous virulence factors, which include surface-associated proteins that allow the bacterium to adhere to eukaryotic cell membranes, a capsular polysaccharide (CP) that protects it from opsonophagocytosis, and several exotoxins. *S. aureus* causes disease mainly through the production of secreted virulence factors such as hemolysins, enterotoxins and toxic shock syndrome toxin. The two main purposes of these secreted virulence factors is to 1) suppress the immune response by inactivating many immunological mechanisms in the host, and 2) cause tissue destruction and help establish the infection. The latter is accomplished by a group of pore forming toxins, the most prominent of which is alpha-hemolysin, also referred to as "alpha-toxin" or "Hla". Alpha-hemolysin is present in the majority of pathogenic strains of *S. aureus*. Multiple studies show that alpha-hemolysin is a key virulence factor for *S. aureus* pneumonia. In this respect, proof of concept studies in mice using point mutants or deletion mutants show that vaccination against this protein provides protection against lethal pneumonia challenge. (Bubeck-Wardenburg, *J Exp Med.*; 205(2):287-94, 2008; Bramley A J., *Infect Immun.*; 57(8):2489-94, 1989; Patel A H. *Infect Immun.*; 55(12):3103-10, 1987).

Anti-alpha-toxin immunity has been shown to be protective in neutralizing detrimental and lethal effects of alpha toxin in experimental models. However, alpha-hemolysin cannot be used as a vaccine in its wild type form due to its toxic effect. While chemical and molecular modifications of alpha-toxin reportedly can reduce its toxicity, no single reported modification entirely eliminates the toxicity of alpha-toxin, while maintaining immunogenicity.

Accordingly, there remains a need in the art for compositions and methods that can safely confer immunity to alpha-hemolysin-expressing *S. aureus*.

SUMMARY OF THE INVENTION

The present invention provides methods of inducing an immune response against an alpha-hemolysin-expressing *S. aureus*, methods of preventing or treating *S. aureus* infections, and composition for preventing or treating *S. aureus* infections.

In one embodiment, the present invention is directed to an isolated oligopeptide at least 55 amino acids in length but no more than 100 amino acids in length, comprising a first amino acid sequence at least 85%, 90%, 95%, or 100% identical to amino acids 27-88 of SEQ ID NO:2.

In another embodiment, the invention is directed to an isolated oligopeptide as described herein, further comprising a second amino acid sequence identical to amino acids 249-262 of SEQ ID NO:2, except for up to one, two, three, four, or five single amino acid substitutions, insertions, or deletions. Also included is an isolated oligopeptide as described above, in which the second amino acid sequence is identical to amino acids 249-262 of SEQ ID NO:2.

The present invention further includes an isolated oligopeptide as described herein, comprising a linker between said first amino acid sequence and said second amino acid sequence. In certain embodiments, the linker comprises polyglycine, e.g., GGG.

The present invention is also directed to an isolated oligopeptide as described herein having calculated molecular energy of less than −2000 kcal/mol, or less than −3500 kcal/mol, or between −4500 kcal/mol and −3000 kcal/mol, or between −4200 kcal/mol and −3500 kcal/mol, or between −3800 kcal/mol and −3600 kcal/mol, or between −4100 kcal/mol and −3900 kcal/mol.

In some embodiments, the present invention includes an isolated oligopeptide as described herein further comprising a heterologous amino acid sequence.

In some embodiments, the present invention includes an isolated oligopeptide as described herein further comprising an immunogenic carbohydrate, e.g., a saccharide. In one embodiment, the immunogenic carbohydrate is a capsular polysaccharide or a surface polysaccharide, e.g., capsular polysaccharide (CP) serotype 5 (CP5), CP8, poly-N-acetylglucosamine (PNAG), poly-N-succinyl glucosamine (PNSG), Wall Teichoic Acid (WTA), Lipoteichoic acid (LTA), a fragment of any of said immunogenic carbohydrates, or a combination of two or more of said immunogenic carbohydrates.

In some embodiments, the present invention includes an isolated oligopeptide as described herein conjugated to an immunogenic carbohydrate.

The present invention further includes an isolated polynucleotide comprising a nucleic acid which encodes an oligopeptide as described herein. The polynucleotide in some embodiments further comprises a heterologous nucleic acid. In another embodiment a heterologous nucleic acid described above comprises a promoter operably associated with said nucleic acid encoding oligopeptide as described herein.

Also included is a vector comprising the polynucleotide as described above or a host cell comprising the vector. In certain embodiments, the invention includes a method of producing an oligopeptide, comprising culturing the host cell and recovering the oligopeptide. The present invention further includes a composition comprising any of the above described oligopeptides. The composition can further comprise an adjuvant. In another embodiment, the composition can further comprise an additional immunogen, e.g., a bacterial antigen. In certain embodiments, the bacterial antigen is a pore forming toxin, a superantigen, a cell surface protein, a fragment of any of said bacterial antigens, or a combination of two or more of said bacterial antigens.

In one embodiment, the invention is directed to a method of inducing an immune response against alpha-hemolysin-expressing S. aureus, comprising administering to a subject in need of said immune response an effective amount of the composition described herein. In one embodiment, the immune response is an antibody response. In another embodiment the immune response is a T cell response. The immune response can also be T-cell response and an antibody response jointly.

In another embodiment, the invention is directed to a method to prevent S. aureus infection or treat a disease caused by a S. aureus infection in a subject comprising administering to a subject in need thereof the composition as described herein. The infection can be skin infection and the disease can be pneumonia or sepsis. The subject can be an animal, a vertebrate, a mammal, a human or a cow. The composition described herein can be administered via intramuscular injection, intradermal injection, subcutaneous injection, intravenous injection, oral administration, mucosal administration, intranasal administration, or pulmonary administration.

Another embodiment of the invention is directed to an isolated antibody or antigen-binding fragment thereof that binds to an epitope in the domain spanning amino acids 27-88 of SEQ ID NO:2. In certain embodiments, the antibody or antigen-binding fragment thereof inhibits alpha-toxin (Hla) oligomerization and/or neutralizes alpha-toxin (Hla). Another aspect of the invention is directed to a composition comprising an antibody or antigen-binding fragment thereof described herein and a carrier. In one embodiment, the composition of the invention comprises a second antibody, e.g., an antibody that binds a bacterial antigen.

The present invention further includes a method for passively immunizing an animal comprising administering an effective amount of any composition described herein to said animal, e.g., a mammal.

Also included is a method of producing a vaccine against S. aureus infection comprising isolating an oligopeptide described herein and adding an adjuvant to the oligopeptide.

The sequence identifiers used herein are as follows:

SEQ ID NO:1: Exemplary full length wild-type S. aureus alpha-hemolysin nucleotide sequence.

SEQ ID NO:2: Exemplary full length wild-type S. aureus alpha-hemolysin amino acid sequence. (GenBank Accession Number YP_001574996.1).

SEQ ID NO:3: Nucleotide sequence encoding "met-AHL62-leu-glu-his$_6$," an oligopeptide comprising amino acids 27-88 of SEQ ID NO:2, an added N-terminal methionine, an added C-terminal leucine and glutamic acid (introduced via Xho I restriction enzyme site); and an added six histidine residues (his$_6$) included in the pET-24a(+) expression vector.

SEQ ID NO:4: Alpha-hemolysin oligopeptide "met-AHL62-leu-glu-his$_6$," comprising amino acids 27-88 of SEQ ID NO:2, an added N-terminal methionine, an added C-terminal leucine and glutamic acid (introduced via Xho I restriction enzyme site), and an added six histidine residues (his$_6$) included in the pET-24a(+) expression vector.

SEQ ID NO:5: Nucleotide sequence encoding "met-AHL79-leu-glu-his$_6$," an oligopeptide comprising amino acids (27-88 of SEQ ID NO:2)-(GGG)-(249-262 of SEQ ID NO:2), an added N-terminal methionine, and an added C-terminal leucine and glutamic acid (introduced via Xho I restriction enzyme site); and an added six histidine residues (his$_6$) included in the pET-24a(+) expression vector.

SEQ ID NO:6: Alpha-hemolysin oligopeptide "met-AHL79-leu-glu-his$_6$," comprising amino acids (27-88 of SEQ ID NO:2)-(GGG)-(249-262 of SEQ ID NO:2), an added N-terminal methionine, an added C-terminal leucine and glutamic acid (introduced via Xho I restriction enzyme site); and an added six histidine residues (his$_6$) included in the pET-24a(+) expression vector.

SEQ ID NO:7: Forward primer.
SEQ ID NO:8: Reverse primer.

DETAILED DESCRIPTION OF THE INVENTION

Figure 1:
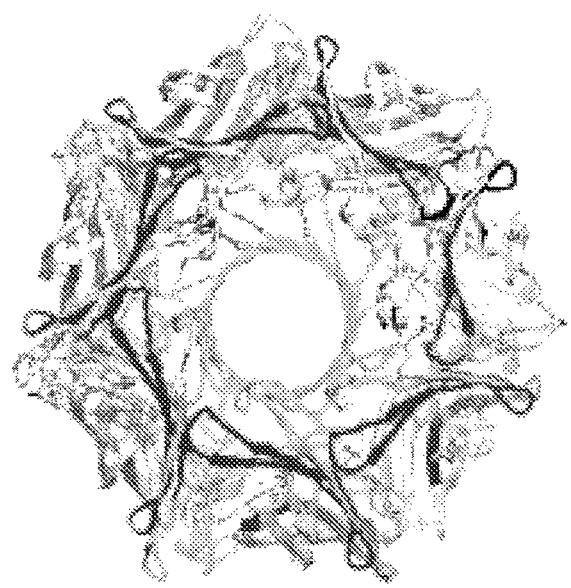
FIG. 1—Alpha-hemolysin heptamer crystal structure rendered in grey ribbon with black ribbons depicting the 4-strand sheet structure from which the constructs described herein are derived.
Figure 2:
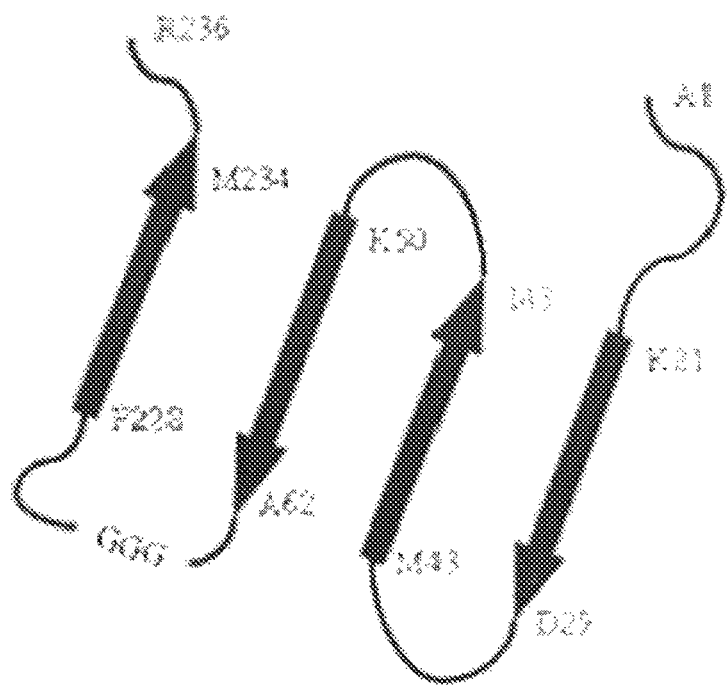
FIG. 2—Topology of the secondary structural elements in alpha-hemolysin for oligopeptides of the invention.

The present invention is directed to alpha-hemolysin-derived oligopeptides and polynucleotides from Staphylococcus, compositions comprising the oligopeptides, and methods of administering the compositions to treat Staphylococcus, e.g., S. aureus infection.

Abbreviations

Standard abbreviations for nucleotides and amino acids are used in this specification. In addition, the following abbreviations are also used herein.

| | |
|---|---|
| AA | Amino acid |
| Å | Angstrom |
| ELISA | Enzyme-Linked-Immunosorbent Serologic Assay |
| HRP | Horse-Radish Peroxidase |
| IPTG | Isopropyl-beta-D-thiogalactoside |
| LB | Luria Bertani (medium) |
| PAGE | Polyacrylamide Gel Electrophoresis |
| PBS | Phosphate Buffered Saline |
| SDS | Sodium Dodecyl Sulfate |
| TMB | (3,3',5,5'-tetramethylbenzidine) |
| SA | S. aureus |
| CP5 | capsular polysaccharide (CP) serotype 5 |
| CP8 | capsular polysaccharide (CP) serotype 8 |
| PNAG | poly-N-acetylglucosamine |
| PNSG | poly-N-succinyl glucosamine |
| WTA | Wall Teichoic Acid |
| LTA | Lipoteichoic acid |

DEFINITIONS

It is to be noted that the term "a" or "an" entity refers to one or more of that entity; for example, "a polynucleotide," is understood to represent one or more polynucleotides. As such, the terms "a" (or "an"), "one or more," and "at least one" can be used interchangeably herein.

The terms "nucleic acid" or "nucleic acid fragment" refers to any one or more nucleic acid segments, e.g., DNA or RNA fragments, present in a polynucleotide or construct. Two or more nucleic acids of the present invention can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide." a "protein," an "amino acid chain," an "amino acid sequence," or any other term used to refer to a chain or chains of two or more amino acids, are included in the definition of a "polypeptide," (even though each of these terms can have a more specific meaning) and the term "polypeptide" can be used instead of or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The term "*S. aureus* alpha-hemolysin polypeptide," as used herein, encompasses full length alpha-hemolysin, and fragments, variants or derivatives of full length alpha-hemolysin, and chimeric and fusion polypeptides comprising full length alpha-hemolysin or one or more fragments of full length alpha-hemolysin.

The terms "fragment," "analog," "derivative," or "variant" when referring to *S. aureus* alpha-hemolysin polypeptides of the present invention include any polypeptides which retain at least some of the immunogenicity or antigenicity of the naturally-occurring proteins. A fragment of *S. aureus* alpha-hemolysin polypeptides of the present invention include proteolytic fragments, deletion fragments and in particular, fragments of alpha-hemolysin polypeptides which exhibit increased solubility during expression, purification, and or administration to an animal. Fragments of alpha-hemolysin further include proteolytic fragments or deletion fragments which exhibit reduced pathogenicity when delivered to a subject. Polypeptide fragments further include any portion of the polypeptide which comprises an antigenic or immunogenic epitope of the native polypeptide, including linear as well as three-dimensional epitopes.

An "epitopic fragment" of a polypeptide antigen is a portion of the antigen that contains an epitope. An "epitopic fragment" can, but need not, contain amino acid sequence in addition to one or more epitopes.

The term "variant," as used herein, refers to an oligopeptide that differs from the recited oligopeptide due to amino acid substitutions, deletions, insertions, and/or modifications. Non-naturally occurring variants can be produced using art-known mutagenesis techniques. In some embodiments, variant polypeptides differ from an identified sequence by substitution, deletion or addition of three amino acids or fewer. Such variants can generally be identified by modifying an oligopeptide sequence, and evaluating the antigenic properties of the modified polypeptide using, for example, the representative procedures described herein.

Polypeptide variants disclosed herein exhibit at least about 85%, 90%, 94%, 95%, 96%, 97%, 98%, 99% or 99.9% sequence identity with identified oligopeptides. Variant polypeptides can comprise conservative or non-conservative amino acid substitutions, deletions or insertions. Derivatives of *S. aureus* alpha-hemolysin oligopeptides of the present invention are polypeptides which have been altered so as to exhibit additional features not found on the native polypeptide. Examples include fusion proteins. An analog is another form of a *S. aureus* alpha-hemolysin polypeptide of the present invention. An example is a proprotein which can be activated by cleavage of the proprotein to produce an active mature polypeptide.

Variants can also, or alternatively, contain other modifications, whereby, for example, an oligopeptide can be conjugated or coupled, e.g., fused to a heterologous amino acid sequence, e.g., a signal (or leader) sequence at the N-terminal end of the protein which co-translationally or post-translationally directs transfer of the protein. The oligopeptide can also be conjugated or produced coupled to a linker or other sequence for ease of synthesis, purification or identification of the polypeptide (e.g., 6-His), or to enhance binding of the polypeptide to a solid support. For example, the oligopeptide can be conjugated or coupled to an immunoglobulin Fc region. The oligopeptide can also be conjugated or coupled to a sequence that imparts or modulates the immune response to the polypeptide (e.g. a T-cell epitope, B-cell epitope, cytokine, chemokine, etc.) and/or enhances uptake and/or processing of the polypeptide by antigen presenting cells or other immune system cells. The oligopeptide can also be conjugated or coupled to other polypeptides/epitopes from *Staphylococcus* sp. and/or from other bacteria and/or other viruses to generate a hybrid immunogenic protein that alone or in combination with various adjuvants can elicit protective immunity to other pathogenic organisms. The polypeptide can also be conjugated or coupled to moieties which confer greater stability or improve half life such as, but not limited to albumin, an immunoglobulin Fc region, polyethylene glycol (PEG), and the like. The oligopeptide can also be conjugated or coupled to moieties (e.g., immunogenic carbohydrates, e.g., a capsular polysaccharide or a surface polysaccharide) from *Staphylococcus* sp. and/or from other bacteria and/or other viruses to generate a modified immunogenic protein that alone or in combination with one or more adjuvants can enhance and/or synergize protective immunity. In certain embodiments, the oligopeptide of the invention further comprises an immunogenic carbohydrate. In one embodiment, the immunogenic carbohydrate is a saccharide.

The term "saccharide" throughout this specification may indicate polysaccharide or oligosaccharide and includes both. Polysaccharides of the invention can be isolated from bacteria and can be sized by known methods. For example, full length polysaccharides can be "sized" (e.g., their size can be reduced by various methods such as acid hydrolysis treatment, hydrogen peroxide treatment, sizing by EMULSIFLEX® followed by a hydrogen peroxide treatment to generate oligosaccharide fragments or microfluidization). Polysaccharides can be sized in order to reduce viscosity in polysaccharide samples and/or to improve filterability for conjugated products. Oligosaccharides have a low number of repeat units (e.g., 5-30 repeat units) and are typically hydrolysed polysaccharides. Polysaccharides of the invention can be produced recombinantly.

S. aureus capsular antigens are surface associated, limited in antigenic specificity, and highly conserved among clinical isolates. In one embodiment, the immunogenic carbohydrate of the invention is a capsular polysaccharides (CP) of S. aureus. In one embodiment, a capsular saccharide can be a full length polysaccharide, however in other embodiments it can be one oligosaccharide unit, or a shorter than native length saccharide chain of repeating oligosaccharide units. Serotyping studies of staphylococcal isolates have revealed several putative capsular serotypes, with types 5 and 8 (CP5 and CP8) being the most prevalent among isolates from clinical infections, accounting for about 25% and 50% of isolates recovered from humans, respectively (O'Riordan and Lee, Clinical Microbiology Reviews, January 2004, p. 218-234, Vol. 17, No. 1; Poutrel and Sutra, J Clin Microbiol. 1993 February; 31(2):467-9). The same isolates were also recovered from poultry, cows, horses and pigs (Tollersrud et al., J Clin Microbiol. 2000 August; 38(8):2998-3003; Cunnion K M et al., Infect Immun. 2001 November; 69(11):6796-803). Type 5 and 8 capsular polysaccharides purified from the prototype strains Reynolds and Becker, respectively, are structurally very similar to each other and to the capsule made by strain T, described previously by Wu and Park (Wu and Park. 1971. J. Bacteriol. 108:874-884). Type 5 has the structure (→4)-3-O-Ac-β-D-ManNAcA-(1→4)-α-L-FucNAc-(1→3)-β-D-FucNAc-(1→)$_n$ (Fournier, J. M., et al., 1987. Ann. Inst. Pasteur Microbiol. 138:561-567; Moreau, M., et al., 1990. Carbohydr. Res. 201:285-297), and type 8 has the structure (→3)-4-O-Ac-β-D-ManNAcA-(1→3)-α-L-FucNAc-(1→3)-β-D-FucNAc-(1→)$_n$ (Fournier, J. M., et al., 1984. Infect. Immun. 45:87-93). Type 5 and 8 polysaccharides differ only in the linkages between the sugars and in the sites of O-acetylation of the mannosaminuronic acid residues, yet they are serologically distinct.

Type 5 and 8 CP conjugated to a detoxified recombinant Pseudomonas aeruginosa exotoxin A carrier were shown to be highly immunogenic and protective in a mouse model (A Fattom et al., Infect Immun. 1993 March; 61(3): 1023-1032; A Fattom et al., Infect Immun. 1996 May; 64(5): 1659-1665) and passive transfer of the CP5-specific antibodies from the immunized animals induced protection against systemic infection in mice (Lee et al., Infect Immun. 1997 October; 65(10): 4146-4151) and against endocarditis in rats challenged with a serotype 5 S. aureus (Shinefield H et al., N Engl J Med. 2002 Feb. 14; 346(7):491-6). A bivalent CP5 and CP8 conjugate vaccine (StaphVAX®, Nabi Biopharmaceutical) was developed that provided 75% protection in mice against S. aureus challenge. The vaccine has been tested on humans (Fattom A I et al., Vaccine. 2004 Feb. 17; 22(7):880-7; Maira-Litrán T et al., Infect Immun. 2005 October; 73(10):6752-62). In certain embodiments, the oligopeptide of the invention is combined with or conjugated to an immunogenic carbohydrate (e.g., CP5, CP8, a CP fragment or a combination thereof).

Immunization with poly-N-acetylglucosamine (PNAG) (McKenney D. et al., Science. 1999 May 28; 284(5419): 1523-7) or poly-N-succinyl glucosamine (PNSG) (Tuchscherr L P. et al., Infect Immun. 2008 December; 76(12): 5738-44. Epub 2008 Sep. 22), both S. aureus surface carbohydrates, has been shown to generate at least partial protection against S. aureus challenge in experimental animal models PNSG was identified as the chemical form of the S. epidermidis capsular polysaccharide/adhesin (PS/A) which mediates adherence of coagulase-negative staphylococci (CoNS) to biomaterials, serves as the capsule for strains of CoNS that express PS/A, and is a target for protective antibodies. PNSG is also made by S. aureus, where it is an environmentally regulated, in vivo-expressed surface polysaccharide and similarly serves as a target for protective immunity (McKenney D. et al., J. Biotechnol. 2000 Sep. 29; 83(1-2):37-44). In certain embodiments, the immunogenic carbohydrate is a surface polysaccharide, e.g., poly-N-acetylglucosamine (PNAG), poly-N-succinyl glucosamine (PNSG), a surface polysaccharide fragment or a combination thereof.

Wall Teichoic Acid (WTA) is a prominent polysaccharide widely expressed on S. aureus strains (Neuhaus, F. C. and J. Baddiley, Microbiol Mol Biol Rev, 2003. 67(4): p. 686-723) and antisera to WTA have been shown to induce opsonophagocytic killing alone and in presence of complement ((Thakker, M., et al., Infect Immun, 1998. 66(11): p. 5183-9), and Fattom et al, U.S. Pat. No. 7,754,225). WTA is linked to peptidoglycans and protrudes through the cell wall becoming prominently exposed on non-encapsulated strains such as USA300 responsible for most cases of community acquired MRSA (CA MRSA) in the US (Hidron, A. I., et al., Lancet Infect Dis, 2009. 9(6): p. 384-92).

Lipoteichoic acid (LTA) is a constituent of the cell wall of Gram-positive bacteria, e.g., Staphylococcus aureus. LTA may bind to target cells non-specifically through membrane phospholipids, or specifically to CD14 and to Toll-like receptors. Target-bound LTA can interact with circulating antibodies and activate the complement cascade to induce a passive immune kill phenomenon. It also triggers the release from neutrophils and macrophages of reactive oxygen and nitrogen species, acid hydrolases, highly cationic proteinases, bactericidal cationic peptides, growth factors, and cytotoxic cytokines, which may act in synergy to amplify cell damage.

In one embodiment, a surface polysaccharide is combined with or conjugated to an oligopeptide of the invention. In certain embodiments the surface polysaccharide is, e.g., poly-N-acetylglucosamine (PNAG), poly-N-succinyl glucosamine (PNSG), Wall Teichoic Acid (WTA), Lipoteichoic acid (LTA), a fragment of any of said surface polysaccharides, or a combination of two or more of said surface polysaccharides.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window (e.g., SEQ ID NO:2 and a homologous polypeptide from another *S. aureus* isolate). In order to optimally align sequences for comparison, the portion of a polynucleotide or polypeptide sequence in the comparison window can comprise additions or deletions termed gaps while the reference sequence (e.g., SEQ ID NO:2) is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The term "epitope," as used herein, refers to portions of a polypeptide having antigenic or immunogenic activity in an animal, for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind its antigen as determined by any method well known in the art. Immunospecific binding excludes non-specific binding but does not necessarily exclude cross-reactivity with other antigens. Whereas all immunogenic epitopes are antigenic, antigenic epitopes need not be immunogenic.

As used herein, the term "antibody" is meant to refer to complete, intact antibodies, antigen-binding fragments, immunospecific fragments, variants, or derivatives thereof of the invention, which include, but are not limited to, polyclonal, monoclonal, multispecific, human, humanized, primatized, murinized or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to antibodies disclosed herein). Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Various forms of antibodies can be produced using standard recombinant DNA techniques (Winter and Milstein, *Nature* 349: 293-99, 1991). In certain embodiments, the antibody of the invention is polyclonal and binds to an oligopeptide described herein.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host. Various species exhibit particular bias for certain codons of a particular amino acid.

The term "composition," or "pharmaceutical composition" can include compositions containing immunogenic oligopeptides of the invention along with e.g., adjuvants or pharmaceutically acceptable carriers, excipients, or diluents, which are administered to an individual already suffering from *S. aureus* infection or an individual in need of immunization against *S. aureus* infection.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the oligopeptide, polynucleotides, compositions, and vaccines of the present invention are pharmaceutically acceptable.

An "effective amount" is an amount wherein the administration of which to an individual, either in a single dose or as part of a series, is effective for treatment or prevention. An amount is effective, for example, when its administration results in a reduced incidence of *S. aureus* infection relative to an untreated individual, as determined, e.g., after infection or challenge with infectious *S. aureus*, including, but is not limited to reduced bacteremia, reduced toxemia, reduced sepsis, reduced symptoms, increased immune response, modulated immune response, or reduced time required for recovery. This amount varies depending upon the health and physical condition of the individual to be treated, the taxonomic group of individual to be treated (e.g. human, nonhuman primate, primate, etc.), the responsive capacity of the individual's immune system, the extent of treatment or protection desired, the formulation of the vaccine, a professional assessment of the medical situation, and other relevant factors. It is expected that the effective amount will fall in a relatively broad range that can be determined through routine trials. Typically a single dose is from about 10 µg to 10 mg/kg body weight of purified oligopeptide or an amount of a modified carrier organism or virus, or a fragment or remnant thereof, sufficient to provide a comparable quantity of recombinantly expressed alpha-hemolysin oligopeptide. The term "peptide vaccine" or "subunit vaccine" refers to a composition comprising one or more oligopeptides of the present invention, which when administered to an animal are useful in stimulating an immune response against *S. aureus* infection.

The term "subject" is meant any subject or individual, particularly a mammalian subject, for whom diagnosis, prognosis, immunization, or therapy is desired. Mammalian subjects include, but are not limited to, humans, domestic animals, farm animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In one embodiment, the subject is a human subject. In another embodiment, the subject is a cow. In yet another embodiment, the subject is a canine.

As used herein, "subject in need thereof" refers to an individual for whom it is desirable to treat, i.e., to prevent, cure, retard, or reduce the severity of *S. aureus* disease symptoms, and/or result in no worsening of disease cause by *S. aureus* over a specified period of time.

The terms "priming" or "primary" and "boost" or "boosting" as used herein refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously.

Polypeptides

The present invention is directed to an isolated staphylococcal alpha-hemolysin oligopeptide with enhanced stability, for example, from *S. aureus, S. epidermidis,* or *S. hemolyticus*, for example, an isolated *S. aureus* alpha-hemolysin oligopeptide as described herein. The alpha-hemolysin of *S. aureus* strain *Staphylococcus aureus* subsp. *aureus* USA300_TCH1516 amino acid sequence is available as GenBank Accession Number YP_001574996.1, and is shown here as SEQ ID NO:2:

One embodiment includes a *S. aureus* alpha-hemolysin oligopeptide at least 55, 56, 57, 58, 59, 60, 61, 62, 63, 64, 65, 66, 67, 68, 69, 70, 71, 72, 73, 74, 75, 75, or 76 amino acids in length but no more than 80, 85, 90, 95, 100, 105, 110, 115, 120, 125, 130, 135, 140, 145, 150, 175, or 200 amino acids in length, comprising a first amino acid sequence at least 85%, 90%, 94%, 95%, 96%, 97%, 98%, 99%, or 100% identical to amino acids 27-88 of SEQ ID NO:2.

In another embodiment, the invention is directed to an isolated oligopeptide as described herein, further comprising a second amino acid sequence identical to amino acids 249-262 of SEQ ID NO:2, or identical to amino acids 249-262 of SEQ ID NO:2 except for up to one, two, three, four, or five single amino acid substitutions, insertions, or deletions.

In yet another embodiment, the invention is directed an isolated oligopeptide as described herein, where the second amino acid sequence is situated C-terminal to the first amino acid sequence. Also included is an isolated oligopeptide as described herein, further comprising a linker between the first amino acid sequence and the second amino acid sequence. The linker can be composed of at least one and up to about 15

MKTRIVSSVTTTLLLGSILMNPVANAADSDINIKTGTTDIGSNTTVKTGDLVTYDKENGM

HKKVFYSFIDDKNHNKKLLVIRTKGTIAGQYRVYSEEGANKSGLAWPSAFKVQLQLPDNE

VAQISDYYPRNSIDTKEYMSTLTYGFNGNVTGDDTGKIGGLIGANVSIGHTLKYVQPDFK

TILESPTDKKVGWKVIFNNMVNQNWGPYDRDSWNPVYGNQLFMKTRNGSMKAADNFLDPN

KASSLLSSGFSPDFATVITMDRKASKQQTNIDVIYERVRDDYQLHWTSTNWKGTNTKDKW

IDRSSERYKIDWEKEEMTN.

The amino acid sequence SEQ ID NO:2 comprises a 26-amino acid signal peptide (amino acids 1 to 26, underlined) followed by a 293-amino acid mature polypeptide (total amino acids 319). The nucleotide sequence corresponding to the alpha-hemolysin amino acid sequence above is presented as SEQ ID NO:1:
NCBI Reference Sequence: NC_010079.1 amino acids, for example small, flexible amino acids, for example, serine, alanine, and glycine residues. In one embodiment, the linker comprises a sequence of three-glycine residues ("GGG").

One embodiment includes an isolated oligopeptide consisting of or consisting essentially of amino acids 27-88 of SEQ ID NO:2 (AHL62). One embodiment includes an iso-

```
>gi|161508266:c1171273-1170314 Staphylococcus aureus subsp. aureus
USA300_TCH1516 chromosome, complete genome
ATGAAAACACGTATAGTCAGCTCAGTAACAACAACACTATTGCTAGGTTCCATATTAATGAATCCTGTCG

CTAATGCCGCAGATTCTGATATTAATATTAAAACCGGTACTACAGATATTGGAAGCAATACTACAGTAAA

AACAGGTGATTTAGTCACTTATGATAAAGAAAATGGCATGCACAAAAAAGTATTTTATAGTTTTATCGAT

GATAAAAATCATAATAAAAAACTGCTAGTTATTAGAACGAAAGGTACCATTGCTGGTCAATATAGAGTTT

ATAGCGAAGAAGGTGCTAACAAAAGTGGTTTAGCCTGGCCTTCAGCCTTTAAGGTACAGTTGCAACTACC

TGATAATGAAGTAGCTCAAATATCTGATTACTATCCAAGAAATTCGATTGATACAAAAGAGTATATGAGT

ACTTTAACTTATGGATTCAACGGTAATGTTACTGGTGATGATACAGGAAAAATTGGCGGCCTTATTGGTG

CAAATGTTTCGATTGGTCATACACTGAAATATGTTCAACCTGATTTCAAAACAATTTTAGAGAGCCCAAC

TGATAAAAAAGTAGGCTGGAAAGTGATATTTAACAATATGGTGAATCAAAATTGGGGACCATATGATAGA

GATTCTTGGAACCCGGTATATGGCAATCAACTTTTCATGAAAACTAGAAATGGCTCTATGAAAGCAGCAG

ATAACTTCCTTGATCCTAACAAAGCAAGTTCTCTATTATCTTCAGGGTTTTCACCAGACTTCGCTACAGT

TATTACTATGGATAGAAAAGCATCCAAACAACAAACAAATATAGATGTAATATACGAACGAGTTCGTGAT

GACTACCAATTGCACTGGACTTCAACAAATTGGAAAGGTACCAATACTAAAGATAAATGGATAGATCGTT

CTTCAGAAAGATATAAAAATCGATTGGGAAAAAGAAGAAATGACTTAA
``` lated oligopeptide consisting of or consisting essentially of amino acids 27-88 of SEQ ID NO:2 connected at its C-terminus through a three-glycine linker, to amino acids 249-262 of SEQ ID NO:2 (AHL79). In certain embodiments, an oligopeptide of the present invention as described herein further includes a native N-terminal *S. aureus* alpha-hemolysin signal peptide sequence, or a heterologous signal peptide sequence. In some embodiments, an oligopeptide as described herein further includes a methionine at the N-terminus, a leucine and a glutamic acid at the C-terminus, and an added six histidine residues (his$_6$) included in the pET-24a(+) expression vector (met-AHL62-leu-glu-his$_6$ or met-AHL79-leu-glu-his$_6$). In one embodiment, the present invention is directed to a *S. aureus* oligopeptide comprising, consisting of, or consisting essentially of MADSDINIKTGTTDIGSNT-TVKTGDLVTYDKENGMHKKVFYSFIDDKNHNKKLL VIRTKGTIAGGGGFSPDFATVITMDRLEHHHHHH ("met-AHL79-leu-glu-his$_6$," SEQ ID NO:6)

In another embodiment, the oligopeptide of the present invention can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenyalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, T7gene10, an avidin/streptavidin/Strep-tag complex, trpE, chloramphenicol acetyltransferase, lacZ (β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of a *S. aureus* alpha-hemolysin oligopeptide from a host cell or any useful immunogenic sequence, including but not limited to sequences that encode a T-cell epitope of a microbial pathogen, or other immunogenic proteins and/or epitopes.

In some embodiments, an oligopeptide attached to a heterologous polypeptide can include a peptide linker sequence joining sequences that comprise two or more peptide regions. Suitable peptide linker sequences can be chosen based on their ability to adopt a flexible, extended conformation, or a secondary structure that could interact with joined epitopes, or based on their ability to increase overall solubility of the fusion polypeptide, or based on their lack of electrostatic or water-interaction effects that influence joined peptide regions.

In some embodiments, the oligopeptide is isolated. An "isolated" oligopeptide is one that has been removed from its natural milieu. The term "isolated" does not connote any particular level of purification. Recombinantly produced *S. aureus* alpha-hemolysin oligopeptides expressed in non-native host cells are considered isolated for purposes of the invention, as are oligopeptides which have been separated, fractionated, or partially or substantially purified by any suitable technique, including by filtration, chromatography, centrifugation, and the like.

Production of an oligopeptide can be achieved by culturing a host cell comprising a polynucleotide which operably encodes an oligopeptide, and recovering the oligopeptide. Determining conditions for culturing such a host cell and expressing the polynucleotide are generally specific to the host cell and the expression system and are within the knowledge of one of skill in the art. Likewise, appropriate methods for recovering an oligopeptide are known to those in the art, and include, but are not limited to, chromatography, filtration, precipitation, or centrifugation.

In one embodiment, the present invention is directed to a staphylococcal alpha-hemolysin oligopeptide as described herein having a molecular energy associated with, for example, better immunogenicity, improved conformational stability, improved solubility, or improved half life. In certain embodiments, an alpha-hemolysin oligopeptide comprises a calculated molecular energy of less than −3000 kcal/mol, or less than −3500 kcal/mol, or between −4500 kcal/mol and −3000 kcal/mol, or between −4200 kcal/mol and −3500 kcal/mol, or between −3800 kcal/mol and −3600 kcal/mol, or between −4100 kcal/mol and −3900 kcal/mol. While not being bound by theory, oligopeptides of the present invention comprising reduced molecular energies have increased immunogenicity, for example, by improved conformational stability. According to the present invention, a thermodynamically stable N-terminal alpha-hemolysin fragment is used which comprises a conformationally stable form of the "arm" region of alpha-hemolysin. While again not wishing to be bound by theory, such an immunogenic fragment is believed to be able to induce antibodies which can interfere with the alpha-hemolysin oligomerization, and thus pore formation, in vivo.

Specific calculated molecular energies of *S. aureus* alpha-hemolysin oligopeptides consisting of amino acids 27-76 of SEQ ID NO:2 (Bubeck-Wardenburg et al. WO 2009/029831), amino acids 27-88 of SEQ ID NO:2 (AHL62), or amino acids 27-88 connected to amino acids 249-262 of SEQ ID NO:2 through a three-glycine linker (AHL79) is represented in Table 1. These measurements are explained in detail in the examples section.

TABLE 1

| CALCULATED MOLECULAR ENERGIES FOR IMMUNOGENIC OLIGOPEPTIDES | |
|---|---|
| Oligopeptide comprising: | Energy (kcal/mol) |
| Amino acids 27-76 of SEQ ID NO: 2 | −2989 |
| Amino acids 27-88 of SEQ ID NO: 2 (AHL62) | −3660 |
| Amino acids (27-88 of SEQ ID NO: 2)-(GGG)-(249-262 of SEQ ID NO: 2) (AHL79) | −3953 |

Polynucleotides

The present invention is further directed to an isolated polynucleotide comprising a nucleic acid encoding a staphylococcal alpha-hemolysin oligopeptide with enhanced stability, for example, from *S. aureus*, *S. epidermidis*, or *S. hemolyticus*, for example, an isolated *S. aureus* alpha-hemolysin oligopeptide as described herein. One embodiment includes an isolated polynucleotide comprising a nucleic acid encoding a *S. aureus* alpha-hemolysin oligopeptide at least 55, 56, 57, 58, 59, 60, 61, 62, 63, 64, 65, 66, 67, 68, 69, 70, 71, 72, 73, 74, 75, 75, or 76 amino acids in length but no more than 80, 85, 90, 95, 100, 105, 110, 115, 120, 125, 130, 135, 140, 145, 150, 175, or 200 amino acids in length, comprising a first amino acid sequence at least 85%, 90%, 94%, 95%, 96%, 97%, 98%, 99%, or 100% identical to amino acids 27-88 of SEQ ID NO:2.

In another embodiment, the invention is directed to an isolated polynucleotide comprising a nucleic acid encoding an oligopeptide as described herein, where the oligopeptide further comprises a second amino acid sequence identical to amino acids 249-262 of SEQ ID NO:2, or identical to amino acids 249-262 of SEQ ID NO:2 except for up to one, two, three, four, or five single amino acid substitutions, insertions, or deletions.

In yet another embodiment, the invention is directed an isolated polynucleotide comprising a nucleic acid encoding an oligopeptide as described herein, where the second amino acid sequence is situated C-terminal to the first amino acid sequence. Also included is an isolated polynucleotide comprising a nucleic acid encoding an oligopeptide as described herein, where the oligopeptide further comprises a linker between said first amino acid sequence and said second amino acid sequence. The linker can comprise at least one and up to about 15 amino acids, for example small, flexible amino acids, for example, serine, alanine and/or glycine residues. In one embodiment, the linker comprises a sequence of three-glycine residues.

One embodiment includes an isolated polynucleotide comprising a nucleic acid encoding an oligopeptide comprising, consisting of, or consisting essentially of amino acids 27-88 of SEQ ID NO:2 (AHL62). One embodiment includes an isolated polynucleotide comprising a nucleic acid encoding an oligopeptide comprising, consisting of, or consisting essentially of amino acids 27-88 of SEQ ID NO:2 connected at its C-terminus through a three-glycine linker to amino acids 249-262 of SEQ ID NO:2 (AHL79). In certain embodiments an isolated polynucleotide encoding an oligopeptide of the present invention further includes a nucleic acid encoding a native N-terminal *S. aureus* alpha-hemolysin signal peptide sequence. In some embodiments, the invention is directed to an isolated polynucleotide comprising a nucleic acid encoding an oligopeptide as described herein, where the oligopeptide further comprises a methionine at N-terminus, e.g., met-AHL62 or met-AHL79.

In one embodiment, the present invention is directed an isolated polynucleotide comprising a nucleic acid encoding an *S. aureus* oligopeptide consisting of or consisting essentially of SEQ ID NO:6.

(met-AHL79-leu-glu-his$_6$, SEQ ID NO: 6)

MADSDINIKTGTTDIGSNTTVKTGDLVTYDKENGMHKKVFYSFIDDKNH

NKKLLVIRTKGTIAGGGGFSPDFATVITMDRLEHHHHHH.

In certain embodiments, an isolated polynucleotide of the present invention further comprises non-coding regions such as promoters, operators, or transcription terminators as described elsewhere herein. In some embodiments, the present invention is directed to a polynucleotide as described herein, and further comprising a heterologous nucleic acid. The heterologous nucleic acid can, in some embodiments, encode a heterologous polypeptide fused to an oligopeptide of the invention. For example, an isolated polynucleotide can comprise additional coding regions encoding, e.g., a heterologous polypeptide fused to an oligopeptide as described herein, or coding regions encoding heterologous polypeptides separate from an oligopeptide of the invention such as, but not limited to, selectable markers, additional immunogens, immune enhancers, and the like.

Also provided are expression constructs, vectors, and/or host cells comprising polynucleotides disclosed herein.

An example of an isolated polynucleotide is a recombinant polynucleotide contained in a vector. Further examples of an isolated polynucleotide include recombinant polynucleotides maintained in heterologous host cells or purified (partially or substantially) polynucleotides in solution. In certain embodiments, a polynucleotide is "recombinant." Isolated polynucleotides or nucleic acids can further include such molecules produced synthetically. The relative degree of purity of a polynucleotide or polypeptide of the invention is easily determined by well-known methods.

Codon Optimization

Also included within the scope of the invention are genetically engineered polynucleotides encoding *S. aureus* alpha-hemolysin oligopeptides of the invention as described herein. Modifications of nucleic acids encoding alpha-hemolysin oligopeptides of the invention can readily be accomplished by those skilled in the art, for example, by oligonucleotide-directed site-specific mutagenesis or de novo nucleic acid synthesis.

In some embodiments, the present invention is directed to an isolated polynucleotide comprising a nucleic acid fragment, which encodes an alpha-hemolysin oligopeptide as described herein, where the coding region encoding the oligopeptide has been codon-optimized. As appreciated by one of ordinary skill in the art, various nucleic acid coding regions will encode the same polypeptide due to the redundancy of the genetic code. Deviations in the nucleotide sequence that comprise the codons encoding the amino acids of any polypeptide chain allow for variations in the sequence of the coding region. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 2

THE STANDARD GENETIC CODE

| | T | C | A | G |
|---|---|---|---|---|
| T | TTT Phe (F) | TCT Ser (S) | TAT Tyr (Y) | TGT Cys (C) |
| | TTC " | TCC " | TAC " | TGC |
| | TTA Leu (L) | TCA " | TAA Ter | TGA Ter |
| | TTG " | TCG " | TAG Ter | TGG Trp (W) |
| C | CTT Leu (L) | CCT Pro (P) | CAT His (H) | CGT Arg (R) |
| | CTC " | CCC " | CAC " | CGC " |
| | CTA " | CCA " | CAA Gln (Q) | CGA " |
| | CTG " | CCG " | CAG " | CGG " |
| A | ATT Ile (I) | ACT Thr (T) | ATT Asn (N) | AGT Ser (S) |
| | ATC " | ACC " | AAC " | AGC " |
| | ATA " | ACA " | AAA Lys (K) | AGA Arg (R) |
| | ATG Met (M) | ACG " | AAG " | AGG " |
| G | GTT Val (V) | GCT Ala (A) | GAT Asp (D) | GGT Gly (G) |
| | GTC " | GCC " | GAC " | GGC " |
| | GTA " | GCA " | GAA Glu (E) | GGA " |
| | GTG " | GCG " | GAG " | GGG " |

It is to be appreciated that any polynucleotide that encodes a polypeptide in accordance with the invention falls within the scope of this invention, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms.

Different factors have been proposed to contribute to codon usage preference, including translational selection, GC composition, strand-specific mutational bias, amino acid conservation, protein hydropathy, transcriptional selection and even RNA stability. One factor that determines codon usage is mutational bias that shapes genome, GC composition. This factor is most significant in genomes with extreme base composition: species with high GC content (e.g., gram positive bacteria). Mutational bias is responsible not only for intergenetic difference in codon usage but also for codon usage bias within the same genome (Ermolaeva M, *Curr. Issues Mol. Biol.* 3(4):91-97, 2001).

Codon bias often correlates with the efficiency of translation of messenger RNA (mRNA), which is in turn believed to be dependent on, inter alia, the properties of the codons being translated and the availability of particular transfer (tRNA) molecules. The predominance of selected tRNAs in a cell is generally a reflection of the codons used most frequently in peptide synthesis. Accordingly, genes can be tailored for optimal gene expression in a given organism based on codon optimization.

The present invention relates to a polynucleotide comprising a codon-optimized coding region which encodes an alpha-hemolysin oligopeptide as described herein. The codon usage is adapted for optimized expression in a given prokaryotic or eukaryotic host cell.

Codon-optimized polynucleotides are prepared by incorporating codons preferred for use in the genes of a given species into the DNA sequence. Also provided are polynucleotide expression constructs, vectors, host cells comprising polynucleotides comprising codon-optimized coding regions which encode *S. aureus* alpha-hemolysin oligopeptides as described herein.

Given the large number of gene sequences available for a wide variety of animal, plant and microbial species, it is possible to calculate the relative frequencies of codon usage. Codon usage tables are readily available, for example, at the "Codon Usage Database" located on the world wide web at kazusa.or.jp/codon/ (visited Dec. 12, 2010), and these tables can be adapted in a number of ways. (Nakamura, Y., et al., "Codon usage tabulated from the international DNA sequence databases: status for the year 2000" *Nucl. Acids Res.* 28:292, 2000).

By utilizing available tables, one of ordinary skill in the art can apply the frequencies to any given polypeptide sequence, and produce a nucleic acid fragment of a codon-optimized coding region which encodes a desired polypeptide, but which uses codons optimal for a given species. For example, in some embodiments of the present invention, the coding region is codon-optimized for expression in *E. coli.*

DNA Synthesis

A number of options are available for synthesizing codon optimized coding regions designed by any of the methods described herein, using standard and routine molecular biological manipulations well known to those of ordinary skill in the art. In addition, gene synthesis is readily available commercially.

Vectors and Expression Systems

The present invention further provides a vector comprising a polynucleotide of the present invention. The term "vector," as used herein, refers to e.g., any of a number of nucleic acids into which a desired sequence can be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is farther characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct made up of genetic material (i.e., nucleic acids), in which the genetic material is extrachromosomal and in some instances, replicates autonomously. A polynucleotide can be in a circular or linearized plasmid or in any other sort of vector. Procedures for inserting a nucleotide sequence into a vector, e.g., an expression vector, and transforming or transfecting into an appropriate host cell and cultivating under conditions suitable for expression are generally known in the art.

In accordance with one aspect of the present invention, provided is a vector comprising a nucleic acid sequence encoding an alpha-hemolysin oligopeptide as described herein. In certain embodiments, the vector is an expression vector capable of expressing an alpha-hemolysin oligopeptide of the invention in a suitable host cell. The term "expression vector" refers to a vector that is capable of expressing a polypeptide of the present invention, i.e., the vector sequence contains the regulatory sequences required for transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain embodiments, the host cell is a bacterium, e.g., *E. coli.*

Host cells are genetically engineered (infected, transduced, transformed, or transfected) with vectors of the invention.

Thus, one aspect of the invention is directed to a host cell comprising a vector which contains a polynucleotide of the present invention. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., *E. coli*), transformed with recombinant bacteriophage DNA, plasmid DNA or cosmid DNA. In some embodiments, the plasmids used with *E. coli* use the T7 promoter-driven system regulated by the LacI protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiX174, pBluescript SK, pbsks, pNH8A, pNH16a, pNH18A, pNH46A (Stratagene), ptrc99a, pKK223-3, pKK233-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences which can be operably joined to an inserted nucleotide sequence encoding a *S. aureus* alpha-hemolysin oligopeptides of the invention. As used herein, the term "regulatory sequences" means nucleotide sequences which are necessary for or conducive to the transcription of an inserted sequence coding a *S. aureus* alpha-hemolysin oligopeptide by a host cell and/or which are necessary for or conducive to the translation by a host cell of the resulting transcript into the desired alpha-hemolysin oligopeptide. Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of *E. coli*, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, a polynucleotide of the invention can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are confirmed using restriction mapping, DNA sequence analysis, and/or PCR analysis. Bacterial cells harboring the correct plasmid can be stored as cell banks.

Immunogenic and Pharmaceutical Compositions

The present invention further provides compositions, e.g., immunogenic or pharmaceutical compositions, that contain an effective amount of an alpha-hemolysin oligopeptide of the invention as described herein, or a polynucleotide encoding an oligopeptide of the invention. Compositions of the present invention can further comprise additional immunogenic components, e.g., as a multivalent vaccine, as well as carriers, excipients or adjuvants.

Compositions of the invention can be formulated according to known methods. Suitable preparation methods are described, for example, in *Remington's Pharmaceutical Sciences*, 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the invention can be administered directly to the subject. The subjects to be treated can be animals; in particular, human subjects can be treated.

Carriers that can be used with compositions of the invention are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions of the invention further include one or more adjuvants, a substance added to an immunogenic composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant. The term "immunogenic carrier" as used herein refers to a first moiety, e.g., a polypeptide or fragment, variant, or derivative thereof which enhances the immunogenicity of a second polypeptide or fragment, variant, or derivative thereof.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or Th$_2$ response into a primarily cellular, or Th$_1$ response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions according to the present invention include, but are not limited to: inert carriers, such as alum, bentonite, latex, and acrylic particles; incomplete Freund's adjuvant, complete Freund's adjuvant; aluminum-based salts such as aluminum hydroxide; calcium-based salts; silica or any TLR biological ligand(s). In one embodiment, the adjuvant is aluminum hydroxide (e.g., ALHDROGEL™ wet gel suspension). In one embodiment, the adjuvant is aluminum phosphate. In another embodiment, the adjuvant is IDC-1001, a glucopyranosyl lipid A (GLA) based adjuvant. The amount of adjuvant, how it is formulated, and how it is administered all parameters which are well within the purview of a person of ordinary skill in the art.

In some embodiments, a composition of the invention further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, an oligopeptide of the invention can be incorporated as part of a liposome or other particle, or can be delivered in conjunction with a liposome. Liposomes for use in accordance with the invention can be formed from standard vesicle-forming lipids, which generally include neutral and negatively charged phospholipids and a sterol, such as cholesterol. A composition comprising a liposome or other particulate suspension as well as an oligopeptide of the invention can be administered intravenously, locally, topically, etc. in a dose which varies according to, inter alia, the manner of administration, the polypeptide being delivered, and the stage of the disease being treated.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, an oligopeptides as described herein, often at a concentration of 25%-75%.

For aerosol or mucosal administration, an oligopeptide according to the present invention can be supplied in finely divided form, optionally along with a surfactant and, propellant and/or a mucoadhesive, e.g., chitosan. The surfactant must, of course, be pharmaceutically acceptable, and in some embodiments soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some embodiments 0.25-5% by weight. The balance of the composition is ordinarily propellant, although an atomizer can be used in which no propellant is necessary and other percentages are adjusted accordingly. In some embodiments, the immunogenic oligopeptides can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

The present invention is also directed to a method of producing a composition according to the invention. In some embodiments, the method of producing the composition comprises (a) isolating an alpha-hemolysin oligopeptide according to the present invention; and (b) adding an adjuvant, carrier and/or excipient to the isolated oligopeptide.

In some embodiments, the present invention is also directed to a multivalent vaccine. A multivalent vaccine can comprise an alpha-hemolysin oligopeptide as described herein, or a polynucleotide encoding such an oligopeptide, and one or more additional immunogenic components. Such components can be additional immunogens of the same infectious agent, e.g., *S. aureus*, or can be immunogens derived from other infectious agents which can be effectively, conveniently, or economically administered together. In certain embodiments, an alpha-hemolysin oligopeptide of the present invention can be combined with other toxin or other virulent components based vaccines to make a broad toxin-based multivalent vaccine capable of targeting multiple bacterial virulence determinants. In other embodiments, an alpha-hemolysin oligopeptide of the present invention can be fused to other immunogenic, biologically significant, or protective epitope containing polypeptides to generate multivalent vaccine in a single chain and induce antibodies against all of them. In yet another embodiment, an alpha-hemolysin oligopeptide of the present invention can be fused to one or more T cell epitopes to induce T cell immunity along with anti alpha toxin antibodies. In a further embodiment, an oligopeptide containing composition of the invention further comprises an additional bacterial antigen, e.g., a pore forming toxin, a superantigen, a cell surface protein, a fragment of any of said bacterial antigens or a combination of two or more bacterial antigens.

"Pore forming toxins" (PFTs) are protein toxins, typically produced by bacteria, e.g., *C. septicum* and *S. aureus*, and are usually cytotoxic because they form pores in the membranes of target cells Non-limiting examples of pore forming toxins of the invention include beta-pore-forming toxins (e.g., Panton-valentine leucocidin (PVL), α-hemolysin, and γ-hemolysin) and alpha-pore-forming toxins (e.g., cytolysin A). In one embodiment, an alpha-hemolysin oligopeptide composition of the present invention further comprises a pore forming toxin, e.g., PVL, cytolysin A, α-hemolysin, γ-hemolysin, a subunit or fragment of a pore forming toxin or any combination thereof.

"Superantigens" (SAgs) are a class of antigens which cause nonspecific activation of T-cells resulting in oligoclonal T-cell activation and cytokine release. SAgs can be produced by pathogenic microbes, e.g., viruses, mycoplasms, and bacteria. Anti-CD3 and anti-CD28 antibodies have also been shown to be potent superantigens. Staphylococcal superantigens include, e.g., staphylococcal enterotoxins (e.g., enterotoxin serotypes A-E (SEA-SEE) and SEG-SEQ), classically the common causes of food poisoning and nonmenstrual TSS, and TSS toxin 1 (TSST-1), the cause of both menstrual and nonmenstrual TSS. In one embodiment, an alpha-hemolysin oligopeptide composition of the present invention farther comprises a superantigen, e.g., a Staphylococcal superantigen.

*S. aureus* cells express surface proteins that promote attachment to host proteins such as laminin and fibronectin that form the extracellular matrix of epithelial and endothelial surfaces. In addition, most strains express a fibrin/fibrinogen binding protein (clumping factor) which promotes attachment to blood clots and traumatized tissue. Most strains of *S. aureus* express both fibronectin and fibrinogen-binding proteins. Immunization with staphylococcal surface proteins such as clumping factor A (ClfA), clumping factor B (ClfB), iron-regulated surface determinant B (IsdB) or fibronectin-binding protein (FnBP) together with ClfA has been shown to generate at least partial protection against *S. aureus* challenge in experimental animal models. In one embodiment, an alpha-hemolysin oligopeptide composition of the present invention further comprises a cell surface protein (e.g., a Staphylococcal cell surface protein), a fragment of a cell surface protein or any combination of cell surface proteins.

Methods of Treatment/Prevention and Regimens

Also provided is a method of treating or preventing *Staphylococcus* infection, e.g., *S. aureus* infection or treating or preventing a disease caused by *Staphylococcus*, e.g., *S. aureus*, in a subject comprising administering to a subject in need thereof a composition as described herein comprising an alpha-hemolysin oligopeptide according to the present invention, or polynucleotides, vectors, or host cells encoding same. In certain embodiments, the subject is a vertebrate, e.g., a mammal, e.g., a feline, e.g., canine, e.g., bovine, e.g., a primate, e.g., a human. In some embodiments, the invention is directed to a method of inducing an immune response against an alpha-hemolysin-expressing *Staphylococcus* bacterium, e.g., *S. aureus*, comprising administering to a subject in need of said immune response an effective amount of a composition as described herein comprising an alpha-hemolysin oligopeptide according to the present invention, or polynucleotides, vectors, or host cells encoding same.

In some embodiments, a subject is administered a composition as described herein comprising an alpha-hemolysin oligopeptide according to the present invention, or polynucleotides, vectors, or host cells encoding same prophylactically, e.g., as a prophylactic vaccine, to establish or enhance immunity to *Staphylococcus*, e.g., *S. aureus*, in a healthy animal prior to potential or actual exposure to *Staphylococcus*, e.g., *S. aureus* or contraction of a *Staphylococcus*-related symptom, thus preventing disease, alleviating symptoms, reducing symptoms, or reducing the severity of disease symptoms. In one embodiment the disease is a respiratory disease, e.g., pneumonia. In another embodiment, the disease is sepsis. Other diseases or conditions to be treated or prevented include, but are not limited to, skin infections, wound infections, endocarditis, bone and joint infections, osteomyelitis, and/or meningitis. One or more compositions, oligopeptides, polynucleotides, vectors, or host cells of the present invention can also be used to treat a subject already exposed to *Staphylococcus*, e.g., *S. aureus*, or already suffering from a *Staphylococcus* related symptom to further stimulate the immune system of the animal, thus reducing or eliminating the symptoms associated with that exposure. As defined herein, "treatment of an animal" refers to the use of one or more compositions, oligopeptides, polynucleotides, vectors, or host cells of the present invention to prevent, cure, retard, or reduce the severity of *S. aureus* symptoms in an animal, and/or result in no worsening of *S. aureus* symptoms over a specified period of time. It is not required that any composition, oligopeptide, polynucleotide, a vector, or a host cell of the present invention provides total protection against a staphylococcal infection or totally cure or eliminate all *Staphylococcus* related symptoms.

As used herein, "a subject in need of therapeutic and/or preventative immunity" refers to a subject in which it is desirable to treat, i.e., to prevent, cure, retard, or reduce the severity of *Staphylococcus* related symptoms, and/or result in no worsening of *Staphylococcus* related symptoms over a specified period of time. As used herein, "a subject in need of said immune response" refers to a subject for which an immune response(s) against any of hemolysin, cytolysin, and leukocidin expressing Staphylococcal strains is desired. Also, contemplated is the utilization of these embodiments to treat cross species pandemic or endemic Staphylococcal infections in bovine, canine, feline or any other domesticated vertebrates Treatment with pharmaceutical compositions comprising an immunogenic composition, oligopeptide or polynucleotide of the present invention can occur separately or in conjunction with other treatments, as appropriate.

In therapeutic applications, a composition, oligopeptide or polynucleotide of the invention is administered to a patient in an amount sufficient to elicit an effective innate, humoral and/or cellular response to the *S. aureus* alpha-hemolysin derived oligopeptide to cure or at least partially arrest symptoms and/or complications.

An amount adequate to accomplish this is defined as "therapeutically effective dose" or "unit dose." Amounts effective for this use will depend on, e.g., the polypeptide or polynucleotide composition, the manner of administration, the stage and severity of the disease being treated, the weight and general state of health of the patient, and the judgment of the prescribing physician, but generally range for the initial immunization for oligopeptide vaccines is (that is for therapeutic or prophylactic administration) from about 0.1 µg to about 5000 µg of polypeptide, in some embodiments about 10 µg to about 30 µg, for a 70 kg patient, followed by boosting dosages of from about 1.0 µg to about 1000 µg, in some embodiments 10 µg to about 30 µg, of polypeptide pursuant to a boosting regimen over weeks to months depending upon the patient's response and condition by measuring, for example, antibody levels in the patient's blood.

In non-limiting embodiments, an effective amount of a composition of the invention produces an elevation of antibody titer to at least 2, 5, 10, 50, 100, 500, 1000, 5000, 10^4, 5×10^4, or 10^5 times the antibody titer prior to administration.

In alternative embodiments, generally for humans the dose range for the initial immunization (that is for therapeutic or prophylactic administration) is from about 1.0 µg to about 20,000 µg of polypeptide for a 70 kg patient, in some embodiments, 2 µg-, 5 µg-10 µg-, 15 µg-, 20 µg-, 25 µg-, 30 µg-, 40 µg-, or 50 µg-2000 µg, followed by boosting dosages in the same dose range pursuant to a boosting regimen over weeks to months depending upon the patient's response and condition by measuring the antibody or T lymphocyte response in the patient's blood. In a specific, non-limiting embodiment, approximately 0.01 to 2000 µg, or in some embodiments 2 µg to 200 µg or 10 µg to 30 µg, of a polypeptide or polynucleotide of the present invention, or its fragment, derivative variant, or analog is administered to a host.

It must be kept in mind that the oligopeptides and compositions of the present invention can generally be employed in serious disease states, that is, life-threatening or potentially life threatening situations. In such cases, in view of the minimization of extraneous substances and the relative nontoxic nature of the oligopeptides, it is possible and can be felt desirable by the treating physician to administer substantial excesses of these oligopeptide compositions.

For therapeutic use, administration should begin at the first sign of *S. aureus* infection or risk factors. In certain embodiments, the initial dose is followed by boosting doses until, e.g., symptoms are substantially abated and for a period thereafter. In frequent infection, loading doses followed by boosting doses can be required.

In certain embodiments, a composition of the present invention is delivered to a subject by methods described herein, thereby achieving an effective immune response, and/or an effective therapeutic or preventative immune response. Any mode of administration can be used so long as the mode results in the delivery and/or expression of the desired oligopeptide in the desired tissue, in an amount sufficient to generate an immune response to *Staphylococcus*, e.g., *S. aureus*, and/or to generate a prophylactically or therapeutically effective immune response to *Staphylococcus*, e.g., to *S. aureus*, in an animal in need of such response. According to the disclosed methods, a composition of the present invention can be administered by mucosal delivery, transdermal delivery, subcutaneous injection, intravenous injection, oral administration, pulmonary administration, intramuscular (i.m.) administration, or via intraperitoneal injection. Other suitable routes of administration include, but not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired oligopeptide in an amount sufficient to generate an immune response to *Staphylococcus*, e.g., *S. aureus*, and/or to generate a prophylactically or therapeutically effective immune response to *Staphylococcus*, e.g., *S. aureus*, in an animal in need of such response. Administration of the present invention can be by e.g., needle injection, or other delivery or devices known in the art.

In some embodiments, a composition comprising an alpha-hemolysin oligopeptide according to the present invention, or polynucleotides, vectors, or host cells encoding same, stimulate an antibody response or a cell-mediated immune response sufficient for protection of an animal against *Staphylococcus*, e.g., *S. aureus* infection. In other embodiments, a composition comprising an alpha-hemolysin oligopeptide according to the present invention, or polynucleotides, vectors, or host cells encoding same, stimulate both a humoral and a cell-mediated response, the combination of which is sufficient for protection of an animal against *Staphylococcus*, e.g., *S. aureus* infection. In some embodiments, a composition comprising an alpha-hemolysin oligopeptide according to the present invention, or polynucleotides, vectors, or host cells encoding same, further stimulates an innate, an antibody, and/or a cellular immune response.

In some embodiments, a composition comprising an alpha-hemolysin oligopeptide according to the present invention, or polynucleotides, vectors, or host cells encoding same, induce antibody responses to a Staphylococcal, e.g., *S. aureus* alpha-hemolysin. In certain embodiments, components that induce T cell responses (e.g., T cell epitopes) are combined with components such as an oligopeptide of the present invention that primarily induces an antibody response.

The present invention further provides a method for generating, enhancing, or modulating a protective and/or therapeutic immune response to *S. aureus* infection in a subject, comprising administering to a subject in need of therapeutic and/or preventative immunity one or more of the compositions described herein.

The compositions of the present invention can be administered to an animal at any time during the lifecycle of the animal to which it is being administered. In humans, administration of the composition of the present invention can occur, and often advantageously occurs, while other vaccines are being administered, e.g., as a multivalent vaccine as described elsewhere herein.

Furthermore, a composition of the invention can be used in any desired immunization or administration regimen; e.g., in a single administration or alternatively as part of periodic vaccination regimes such as annual vaccinations, or as in a prime-boost regime in which composition or oligopeptide or polynucleotide of the present invention is administered either before or after the administration of the same or of a different oligopeptide or polynucleotide. Recent studies have indicated that a prime-boost protocol is often a suitable method of administering vaccines. In a prime-boost protocol, one or more compositions of the present invention can be utilized in a "prime boost" regimen. An example of a "prime boost" regimen can be found in Yang, Z. et al. *J. Virol.* 77:799-803, 2002, which is incorporated herein by reference in its entirety.

In certain embodiments, a composition comprising an alpha-hemolysin oligopeptide according to the present invention, or polynucleotides, vectors, or host cells encoding same, can be administered to induce a cross-reactive immune response to a bacterium expressing a similar, but not identical pore-forming toxin. By non-limiting example, an oligopeptide of the invention can be administered to treat or prevent infections or diseases caused by staphylococcal species including, but not limited to *S. aureus, S. epidermidis*, and *S. hemolyticus*), streptococcal species, including, but not limited to *Streptococcus pyogenes* and *S. pneumoniae*, enterococcal species, including, but not limited to *Enterococcus faecalis* and *E. faecium*.

Infections to be treated include, but are not limited to a localized or systemic infection of skin, soft tissue, blood, or an organ or an auto-immune disease. Specific diseases or conditions to be treated or prevented include, but are not limited to, respiratory diseases, e.g., pneumonia, sepsis, skin infections, wound infections, endocarditis, bone and joint infections, osteomyelitis, and/or meningitis.

Immune Correlates

A number of animal models for *S. aureus* infection are known in the art and can be used with the methods of present invention without undue experimentation. For example, a hamster model of methicillin-resistant *Staphylococcus aureus* (MRSA) pneumonia has been described for the testing of antimicrobials. (Verghese A. et al., *Chemotherapy.* 34:497-503 (1988), Kephart P A. et al. J Antimicrob *Chemother.* 21:33-9, (1988)). Further, a model of *S. aureus*-induced pneumonia in adult, immunocompetent C57BL/6J mice is described, which closely mimics the clinical and pathological features of pneumonia in human patients. (Bubeck-Wardenburg J. et al., *Infect Immun.* 75:1040-4 (2007)). Additionally, virulence has been tested in a rat model of *S. aureus* pneumonia as described in McElroy et al. (McElroy M C. et al., *Infect Immun.* 67:5541-4 (1999)). Finally, a standardized and reproducible model of MRSA-induced septic pneumonia to evaluate new therapies was established in sheep. (Enkhbaatar P. et al., *Shock* 29(5):642-9, 2008).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Roitt. I., Brostoff, J. and Male D., Immunology, 6$^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

EXAMPLES

Example 1

Molecular Modeling and Design of Vaccine Candidates

This example describes molecular modeling (computer based) techniques for deriving, analyzing and manipulating the structure of alpha-hemolysin in order to design vaccine candidates.

FIG. 1 shows alpha-hemolysin heptamer crystal structure. The functional unit of the toxin is a heptamer in which monomer subunits are packed tightly against each other with an N-terminal stretch of amino acids wrapping around the adjacent subunit holding the structure together. The present invention targets the surface exposed areas of alpha-hemolysin monomer that would be also critical for oligomerization (such as the N-terminal arm) providing an effective strategy to induce multiple antibodies that would interfere with alpha-hemolysin function.

The Discovery Studio 2.5 (Accelrys, Inc) program running on a Dell Precision 690 with Red Hat Enterprise Linux 4 was used to build, visualize, and analyze the protein models. Simulations were performed in vacuo using a distance-dependent dielectric of 1 and nonbonded interactions limited to within 14 Å in a CHARMM force-field. Minimization involved 1000 steps of Smart Minimizer with a RMS gradient of 0.1. The calculated energies of the polypeptide models were determined using a protocol that applied physics-based estimation of the single point energy of each amino acid by quantifying unfavorable and favorable atom-atom contacts with the nonbonded interaction limit of 14 Å (angstroms) using atom-atom interaction values established by the Charmm energy function. The quality of the protein models were continually monitored using the Validate Protein Structure protocol to identify poor or incorrect main chain and side chain conformations for each amino acid. The crystal structure of heptameric alpha-hemolysin (PDB code 7AHL; the structure can be downloaded at pdb.org, last visited Jan. 31, 2011). The template in the model building is disclosed in Song et al., *Science.* 13; 274(5294):1859-66, 1966). Accordingly, two oligopeptide candidates were designed based on structural modeling and medicinal chemistry and tested in mice.

Analysis of *S. aureus* Alpha-Hemolysin Structure

The *S. aureus* alpha-hemolysin protein from strain *Staphylococcus aureus* subsp. *aureus* USA300_TCH1516 was used as a prototype. Its amino acid sequence, i.e., GenBank Accession Number YP_001574996.1 is presented herein as SEQ ID NO:2. This polypeptide comprises a 26-amino acid signal peptide from amino acids 1 to 26, and a mature protein from amino acids 27 to 319. Other alpha-hemolysin proteins, e.g., from other strains of *S. aureus*, or from other staphylococci, or from other bacterial pathogens in general, can be used as a source for deriving immunogenic oligopeptides according to the methods disclosed herein as well.

An oligopeptide consisting of amino acids 27-76 of SEQ ID NO:2, in each of the subunits in the 7AHL crystal structure was identified and clustered into a group for further analysis. FIG. 2 shows topology of the secondary structural elements in alpha-hemolysin for oligopeptides as described herein. This 50-amino acid oligopeptide, comprises the N-terminal loop and two antiparallel β-strands. These two strands were part of a larger secondary structure that consists of an antiparallel 4-strand sheet. Detailed analysis of the crystal structure revealed that immunogenic fusion proteins can be generated from this 4-strand sheet structure.

Calculated Molecular Energies for Immunogenic Fusion Constructs

Amino acids 27-76 of SEQ ID NO:2, were clipped from subunit A of the heptameric alpha-hemolysin 7AHL crystal structure and its molecular energy was calculated as a baseline for comparison to candidate oligopeptides. The first candidate polypeptides were built by extending the amino acids 27-76 of SEQ ID NO:2, by the addition of single amino acids along the alpha-hemolysin oligopeptide sequence and each resulting structure was energy minimized and its molecular energy calculated. The relative stabilities of this series of oligopeptides indicated that the 62-amino acid oligopeptide segment consisting of amino acids 27-88 of SEQ ID NO:2 (AHL62) was an ideal candidate for further immunogenicity studies. Table 1 shows the calculated energy of the oligopeptide segments consisting of amino acids 27-76 of SEQ ID NO:2, and consisting of amino acids 27-88 of SEQ ID NO:2, respectively. Based on their calculated molecular energies, the AHL62 oligopeptide was predicted to be more stable than the oligopeptide segment consisting of amino acids 27-76 of SEQ ID NO:2. Further, the AHL62 oligopeptide provides a larger, ordered binding surface for immunogenic activity due to the fact that it is comprised of a 3-strand sheet structure relative to the 2-strand sheet of the 50-amino acid oligopeptide. Thus, AHL62 was selected as the first oligopeptide construct for in vivo study.

Molecular models were generated by extending the AHL62 linearly along the primary alpha-hemolysin amino acid sequence, but these peptide models resulted a less ordered binding surface for immunogenic activity. Accordingly, extending the 3-strand sheet of AHL62, was extended into a 4-strand sheet that was shown in the 7AHL hemolysin crystal structure was a logical strategy. However, the last strand in this 4-strand sheet includes amino acids 249-262 of SEQ ID NO:2, which is distal in the primary sequence relative to AHL62. Molecular modeling was used to sample different linkers between Ala88 of the third-strand and Gly231 of the fourth strand. The oligopeptide segments consisting of amino acids 27-88 of SEQ ID NO:2 and 249-262 of SEQ ID NO:2 were clipped from subunit A in the 7AHL crystal structure, and different type and length linkers were evaluated. Because of its conformational flexibility and small side chain, glycine residues were selected as the linker units. The number of linker units were selected based on modeling linkers consisting of one to six glycine residues that were covalently attached to residues Ala88 and Gly231. Six different polypeptide models with varying glycine counts in their linker units were generated, and energy minimized. Their molecular energies were calculated to determine and rank order their relative stabilities. The three-glycine linker was shown to be optimal and had a lower calculated molecular energy than the structures of the 50-amino acid and 62-amino acid segments. Thus, the oligopeptide consisting of amino acids 27-88 of SEQ ID NO:2 connected to amino acids 249-262 of SEQ ID NO:2 by a three-glycine linker (AHL79) was selected as a second construct for this study.

Figure 3:
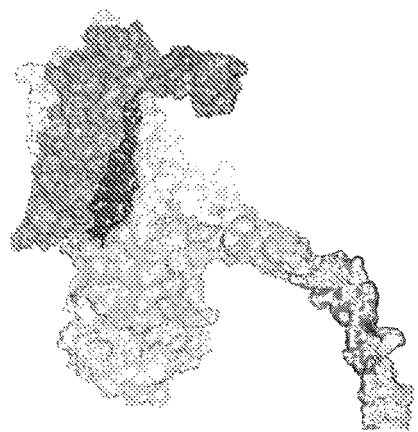
FIG. 3—The relative topology of oligopeptide "AHL62" amino acids 27-88 of SEQ ID NO:2 and oligopeptide "AHL79" amino acids (27-88 of SEQ ID NO:2)-(GGG)-(249-262 of SEQ ID NO:2) on the protein surface of a subunit from the 7AHL heptametrical hemolysin crystal structure. The protein surface for amino acids 27-88 of SEQ ID NO:2 is colored dark grey, and the protein surface for amino acids 249-262 of SEQ ID NO:2 is colored black, and the remaining protein structure is colored light grey.

AHL62 and AHL79 were predicted to be more stable than the 50-amino acid oligopeptide consisting of amino acids 27-76 of SEQ ID NO:2, that was previously shown to be a critical epitope. Furthermore, amino acids 77-88 and 231-241 of SEQ ID NO:2 were predicted to be additive to the epitope. FIG. 3 shows the relative topology of AHL62 and AHL79 on the protein surface of subunit A from the 7AHL heptameric alpha-hemolysin crystal structure.

Example 2

Cloning and Expression of *S. aureus* Alpha-Hemolysin Oligopeptides

This example describes the isolation and cloning of an *S. aureus* alpha-hemolysin gene fragment, as well as the expression of met-AHL62, and met-AHL79, modeled as in Example 1.

A) A nucleic acid fragment encoding an oligopeptide consisting of amino acids 27-76 of SEQ ID NO:2, with an added N-terminal methionine was amplified by PCR amplification of genomic DNA from *S. aureus* strain USA300. Primers used for PCR amplification included synthetic restriction sites, NdeI shown capitalized in the forward primer, SEQ ID NO:7 ttCATATG gcagattctgatattaatattaaaacc and, Xho I shown capitalized in the reverse primer, SEQ ID NO:8 ttCTCGAGtttattatgattttatcatcgataaaac. Vector pET-24a(+) has an artificial sequence coding 6 histidine residues, to facilitate detection and purification of the recombinant protein. After purification using a PCR column, the synthesized fragments, and also expression vector pET-24a(+) (Novagen) were digested with Nde 1 and Xho1 restriction enzymes and gel-purified. The PCR fragment and pET-24a(+) vector were then ligated using rapid ligase (Roche). After ligation, the recombinant expression construct was transformed into BL21 (DE3) *E. coli* cells for clone selection. Antibiotic-resistant clones were picked at random and screened for the presence of alpha-hemolysin-encoding inserts in the proper orientation for expression by conventional restriction endonuclease digestion.

B) Nucleic acid fragments encoding met-AHL62-leu-glu-his$_6$ and met-AHL79-leu-glu-his$_6$ were synthesized and cloned into pET24a(+) by DNA2.0 inc. (Menlo Park, Calif. 94025 USA). The nucleotide sequences of these inserts are presented as SEQ ID NO:3 and SEQ ID NO:5, respectively. A control construct, met-AHL50-leu-glu-his$_6$, was prepared in the same vector.

Figure 4A:
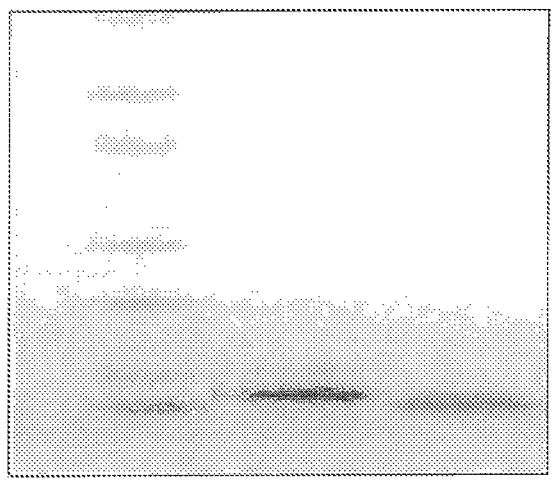
FIGS. 4 (A and B)—(A) SDS-PAGE for met-AHL62-leu-glu-his$_6$ (AHL62AA) and met-AHL79-leu-glu-his$_6$ (AHL79AA) protein from E. coli strain BL21(DE3) with constructs pET24-62AA His$_6$ or pET24-79AA His$_6$ overexpression after IPTG induction. Lane 1: M, molecular weight standards protein size marker; Lane 2: met-AHL79-leu-glu-his$_6$; Lane3: met-AHL62-leu-glu-his$_6$. (B) Western blot analysis by sheep anti-alpha-hemolysin polyclonal antibody (Toxin Technology, Sarasota, Fla.). Lane 1: M, molecular weight standards protein size marker; Lane 2: met-AHL79-leu-glu-his$_6$; Lane3: met-AHL62-leu-glu-his$_6$.
Figure 4B:
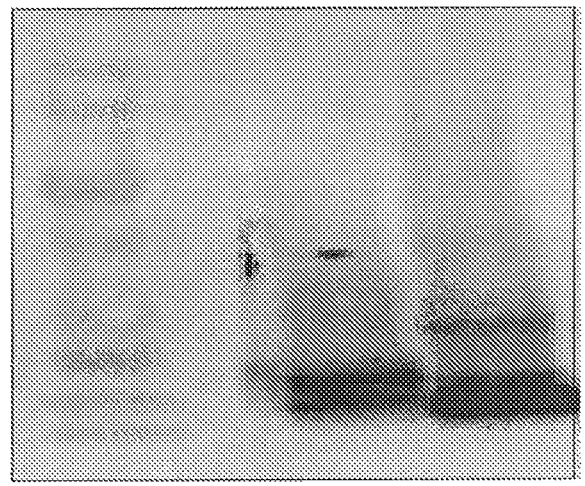

To confirm successful expression of the two oligopeptides, BL21 (DE3) cells with or without the recombinant constructs were cultured in LB medium supplemented with 50 µg/ml kanamycin at 30° C. until a cell density (OD650) of 0.4-0.6 was reached. The cell cultures were then induced with IPTG at 1 mM and grown overnight. The cells were collected and IPTG-inducible expressed proteins were separated based on molecular size via SDS-PAGE (Sodium Dodecyl Sulfate-Polyacrylamide Gel Electrophoresis) using common techniques. FIG. 4A shows SDS-PAGE of the two *S. aureus* oligopeptides, expressed in *E. coli* BL21 cells. The proteins were then subjected to western blot analysis using sheep anti-alpha-hemolysin polyclonal antibody (Toxin Technology, Sarasota, Fla.). FIG. 4B shows the Western blot of the two *S. aureus* oligopeptides, expressed in *E. coli* BL21 cells.

Example 3

Purification and Formulation of Recombinant *S. aureus* Alpha-Hemolysin Oligopeptides for Use in Immunogenic Compositions Recombinant *S. aureus* oligopeptides met-AHL62-leu-glu-his$_6$ and met-AHL79-leu-glu-his$_6$ were expressed in BL21 *E. coli* cells with expression vector pET-24a(+) as described in Example 2. SDS-PAGE analysis was performed to measure the level of protein production. For small scale His-tagged protein purification 'His Spin Trap™ kits (GE Healthcare, Piscataway, N.J.) was used according to the manufacturer's instructions The vaccine was formulated in 10 mM Phosphate buffered Saline (PBS) and stored at −80° C. until use.

Example 4

Evaluation of met-AHL62 and met-AHL79 in a *S. aureus* Pneumonia Animal Model

Six-week old female BALB/c mice (5/group) were immunized intramuscularly (IM) either with met-AHL62-leu-glu-his$_6$ or met-AHL79-leu-glu-his$_6$ in ALHYDROGEL™ on days 0, 14 and 28 in a 0.01 ml volume of PBS. Mice were bled via tail vein incision prior to each immunization and 14 days post last immunization. Blood samples were centrifuged in serum separator tubes and antibody titers in sera were determined by ELISA; briefly, 96-well plates were coated with 1 µg/ml (100 ng/well) of antigen (alpha toxin or met-AHL79) overnight at 4° C. Plates were blocked with 4% milk in PBS for 2 hours at RT. Serum samples were prepared in 1:100 and 1:1000 dilutions in a 96-well plate using 4% milk in PBS as diluent. Plates were washed 3 times, inverted and blotted on paper towels to remove residual liquid and sample dilutions were applied in 100 µl volume/well. Plates were incubated for 2 hours at room temperature (RT) and washed 3 times as described above before applying the conjugate, goat anti-mouse IgG (H&L)-HRP (Horse Radish Peroxidase) in 1% milk in PBS solution (Bio-Rad). Plates were incubated for 1 hour at RT, washed as described above and incubated with TMB (3,3',5,5'-tetramethylbenzidine) to detect HRP for 30 min. Optical density at 650 nm was measured using a Versamax™ plate reader.

Figure 5:
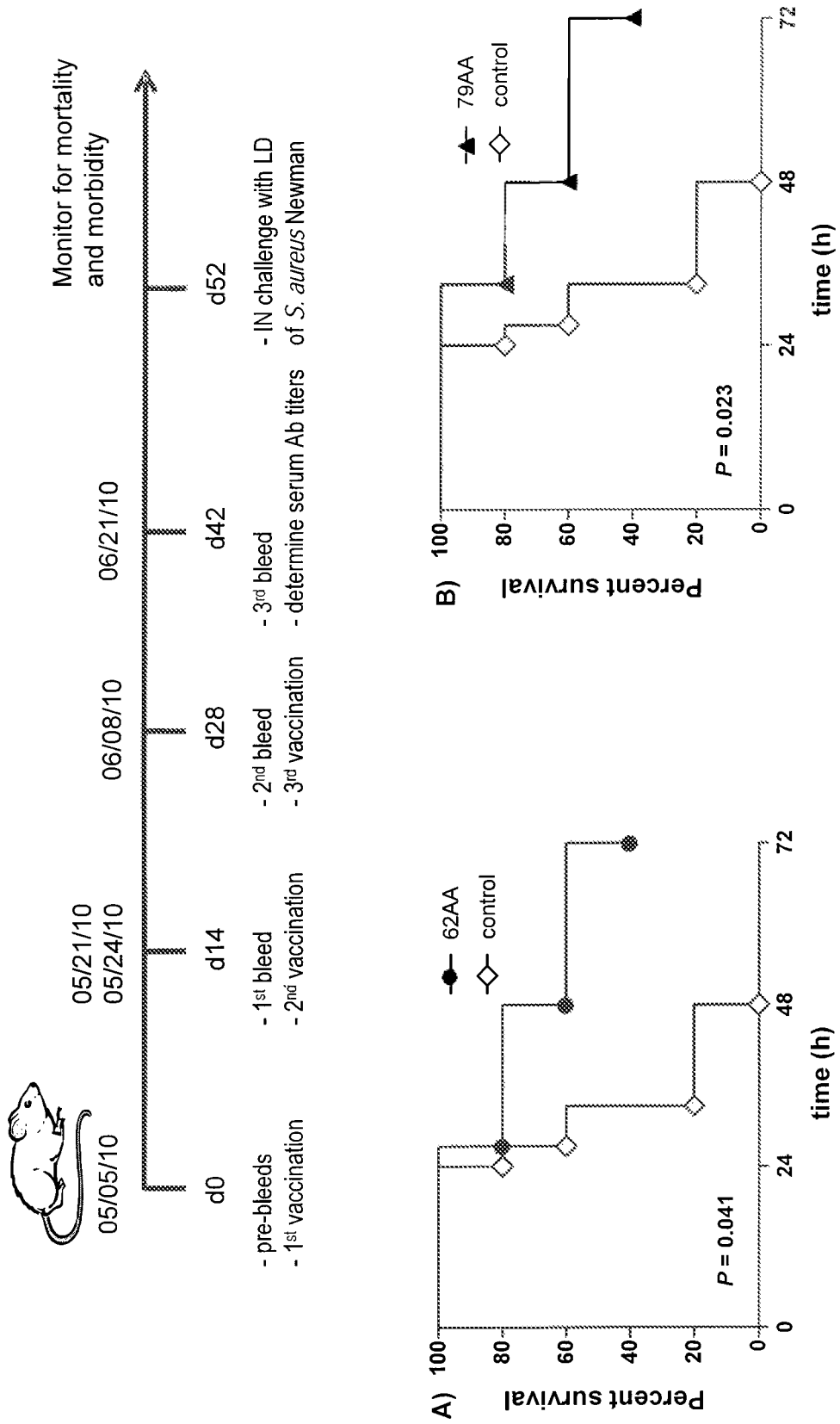
FIGS. 5 (A and B)—Vaccination schedule and percent survival of intramuscularly (IM) immunized vs. non-immunized mice after intranasal (IN) challenge with S. aureus (SA) Newman bacterial strain (SA Newman strain), % survival of mice immunized with (A) met-AHL62-leu-glu-his$_6$ (62AA) or (B) met-AHL79-leu-glu-his$_6$ (79AA) in ALHYDROGEL™.

On day 52 mice were challenged intranasally (IN) with a lethal dose of live *S. aureus* (SA) Newman bacterial strain, which expresses alpha-hemolysin, and animals were monitored for 72 h post challenge for mortality and morbidity (weight loss and symptoms of discomfort). As demonstrated in FIG. 5, mice that were immunized with (A) met-AHL62-leu-glu-his$_6$ or (B) met-AHL79-leu-glu-his$_6$ oligopeptides had significantly higher survival rates than non-immunized mice.

Example 5

Comparison of In Vivo Efficacy of AHL-62aa and AHL-50aa

Figure 6:
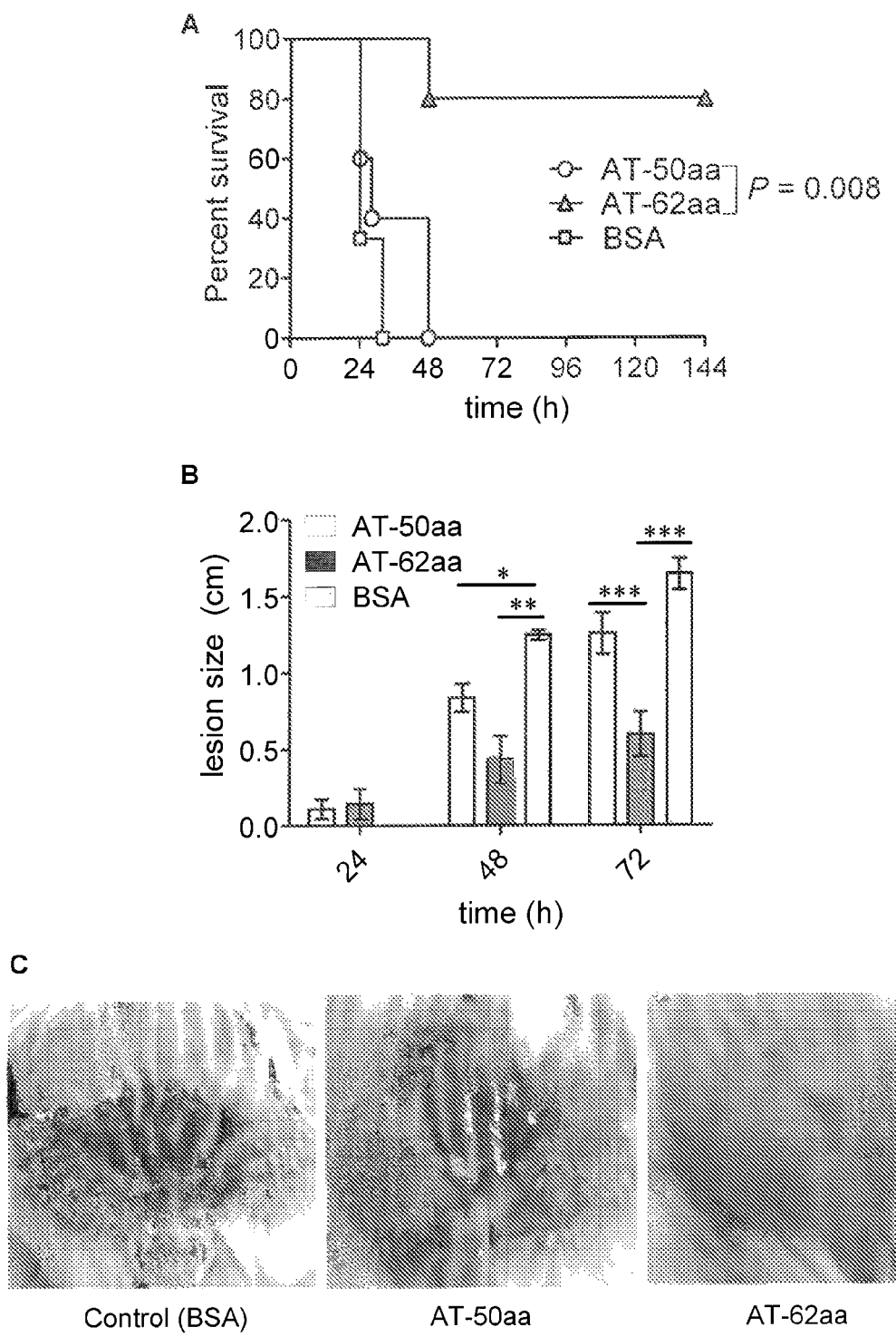
FIGS. 6 (A, B and C)—(A) Percent (%) survival of mice (n=10/group) immunized with 40 μg of met-AHL50-leu-glu-his$_6$ (AT-50aa), met-AHL62-leu-glu-his$_6$ (AT-62aa), or 40 μg BSA in ALHYDROGEL™ after IN challenge with 2×10$^8$ CFU SA Newman strain (P=0.008 using Log-Rank (Mantel-Cox Test)). (B) Lesion size of immunized mice after intradermal (ID) challenge with 5 μg of Hla. Lesion size at different time points post challenge of mice (n=10/group) immunized with 4 μg of AHL-50aa (AT-50aa), AHL-62aa (AT-62aa), or 40 μg BSA. Statistical correlation: Two-way ANOVA and Bonferroni posttests; "*" denotes statistical significance. (C) Images of the dermal lesion of mice immunized with the indicated vaccines and challenged with 5 μg purified Hla.

This example shows a comparative study testing adjuvants that could potentially be used in humans in combination with met-AHL62-leu-glu-his$_6$ (AHL-62aa) and met-AHL50-leu-glu-his$_6$ (AHL-50aa). In this study, ALHYDROGEL™ was used as the adjuvant for evaluation of the vaccine potential of the AHL-62aa and AHL-50aa constructs. Groups of 10 mice were vaccinated intramuscularly (IM) 3× with either 40 µg or 4 µg of AHL-50aa or AHL-62aa adsorbed to ALHYDROGEL™. Two weeks after the last vaccination, mice given 40 µg doses were challenged intranasally (IN) with 2×10$^8$ CFU of SA strain Newman. AHL-62aa provided 80% protection against lethality while control mice died within 24 h (FIG. 6A). In contrast to prior reports using Freund's adjuvant, mice immunized with AHL-50aa/ALHYDROGEL™ only survived for 48 h. A dermal necrosis model was used to evaluate vaccine-mediated protection against purified Hla. Groups of low dose (4 µg) or mock-vaccinated mice were challenged intradermally with 5 µg of purified Hla and observed for 72 h for lesion development. Mice vaccinated with AHL-62aa developed significantly smaller lesions after 72 h than mice vaccinated with AHL-50aa or mock-treated mice (See FIGS. 6B & 6C).

ALHYDROGEL™, aluminum phosphate (E.M. SERGEANT PULP AND CHEMICAL Co, Inc.), and IDC-1001 (Immune Design Corp.) were used as the adjuvants for further evaluation of the vaccine potential of the AHL-62aa oligopeptide. Groups of 5 (BALB/c) mice were immunized intramuscularly (IM) 3× at two week intervals with 5 ug of AHL-62aa formulated either with 35 ug of ALHYDROGEL™ (i.e., Al(OH)$_3$, in 0.01 ml 50 mM TRIS, (Table 3, part (A)), 35 ug of aluminum phosphate (i.e., AlPO$_4$), in 0.01 ml 50 mM TRIS (Table 3, part (B)), 20 ug of IDC-1001 in 0.01 ml PBS (Table 3, part (C)), or 5 ug of AHL-62aa (without adjuvant) in 0.01 ml PBS (Table 3, part (D)). On day 35, mice were bled via tail vein incision for determination of antibody titers. Blood samples were centrifuged in serum separator tubes and mouse sera were analyzed for total and neutralizing antibodies to alpha-toxin (Hla). Total antibody titers were determined by ELISA, as described in Example 4, using full length purified Hla as a coating antigen and eleven semi-log dilutions of sera starting from 1:100 to 1:10,000,000. The ELISA titer (EC$_{50}$) was defined as the dilution of the serum resulting in 50% maximum OD (inflection point of the 4-PL curve). Similarly, the neutralizing titer (NT$_{50}$) was defined as the dilution of the antibody resulting in 50% inhibition of the lysis of rabbit red blood cells (RBC) induced by 1 ug/ml of purified Hla. For NT$_{50}$ assay, serial dilutions of mouse sera were incubated with alpha toxin (0.1 ug/ml) (List Biological Laboratories, Campbell, Calif.) at room temperature for 10 minutes before adding 2% RBC (Colorado serum company, CO) followed by 30 min incubation at 37° C. After incubation cells were pelleted and the absorbance in the supernatant was determined in a VersaMax ELISA, Microplate Reader (Molecular Devices CA) at 416 nm. Neutralization titer 50 (NT$_{50}$) was determined by plotting the OD416 nm in diluted serum samples using a four parameter logistic (4-PL) curve fit. Standard serum samples with high, medium and low NT$_{50}$ were run to the assay during each assay run.

To evaluate the relationship between immunogenicity and protection from lethal challenge, on day 41 mice were challenged intraperitoneally (IP) with 5×10$^4$ CFU of *S. aureus* (SA) USA300 strain in 3% hog mucin, and monitored for morbidity and mortality over 7 days.

Mice immunized with AHL-62aa formulated with 35 ug of ALHYDROGEL™ showed low ELISA titers with a geometric mean of 189 and neutralizing titers below the limit of detection. Consistent with the low antibody titers, 3 out of 5 mice in this group died within 20 hours of challenge (Table 3, part (A)). Mice immunized with AHL-62aa formulated with 35 ug of aluminum phosphate showed higher antibody titers with a geometric mean of 300, and 3 out of 5 mice showed detectable neutralizing titers. All mice in this group survived the challenge (Table 3, part (B)). All mice immunized with AHL-62aa formulated with 20 ug of IDC-1001 showed much higher ELISA and NT50 titers with geometric means of 2476 and 309, respectively. Consistent with the high titers all mice survived the challenge (Table 3, part (C)). Very low ELISA and undetectable NT50 titers were observed in mice immunized with AHL-62aa without adjuvant (Table 3, part (D)). Mice immunized with a control vaccine (recombinant staphylococcal enterotoxin B vaccine; STEBVax; Integrated Bio-Therapeutics, Inc.) along with aluminum hydroxide showed no titer to Hla (Table 3, part (E)). All mice in the two control groups died within 20 hours of challenge with SA USA300 strain.

TABLE 3

Immunogenicity and in vivo efficacy of AHL-62aa and adjuvant combinations

| Adjuvant | Adjuvant dose | Mouse # | ELISA EC$_{50}$ | Neut titer NT$_{50}$ | Time of death |
|---|---|---|---|---|---|
| (A) Al(OH)$_3$ ALHYDROGEL ™ | 35 ug | M1 | 361 | <64. | 20 h |
| | | M2 | 658 | <64. | survived |
| | | M3 | 198 | <64. | 20 h |
| | | M4 | 69 | <64. | 20 h |
| | | M5 | 75 | <64. | survived |
| | | Geo Mean | 189 | <64 | |
| (B) AlPO$_4$ | 35 ug | M1 | 1230 | 127 | survived |
| | | M2 | 18 | <64. | survived |
| | | M3 | 510 | <64. | survived |
| | | M4 | 674 | 127 | survived |
| | | M5 | 320 | 110 | survived |
| | | Geo Mean | 300 | | |
| (C) IDC-1001 | 20 ug | M1 | 1800 | 251 | survived |
| | | M2 | 1630 | 194 | survived |
| | | M3 | 1530 | 159 | survived |
| | | M4 | 2540 | 423 | survived |
| | | M5 | 8170 | 859 | survived |
| | | Geo Mean | 2476 | 309 | |
| (D) No adjuvant | — | M1 | 198 | <64. | 20 h |
| | | M2 | 208 | <64. | 20 h |
| | | M3 | 91.5 | <64. | 20 h |
| | | M4 | 76.7 | <64. | 20 h |
| | | M5 | 307 | <64. | 20 h |
| | | Geo Mean | 155 | <64 | |

TABLE 3-continued

Immunogenicity and in vivo efficacy of AHL-62aa and adjuvant combinations

| Adjuvant | Adjuvant dose | Mouse # | ELISA EC$_{50}$ | Neut titer NT$_{50}$ | Time of death |
|---|---|---|---|---|---|
| (E) Control vaccine (STEBVax) + Al(OH)$_3$ | | M1 | 0 | <64. | 20 h |
| | | M2 | 0 | 120 | 20 h |
| | | M3 | 0 | <64. | 20 h |
| | | M4 | 0 | <64. | 20 h |
| | | M5 | 0 | <64. | 20 h |

Example 6

Polyclonal Anti-AHL-62aa Antibodies Inhibit Alpha-Toxin (Hla) Oligomerization

This example shows a study of the mechanism of action of antibodies triggered by AHL-62aa. Rabbit polyclonal antibodies (pAb) were raised against AHL-62aa and tested in toxin neutralization (TNA) and oligomerization assays. AHL-62aa pAb effectively neutralized 1 µg/ml Hla (NT50: 13.4 µg/ml; see FIG. 7A).

Figure 7:
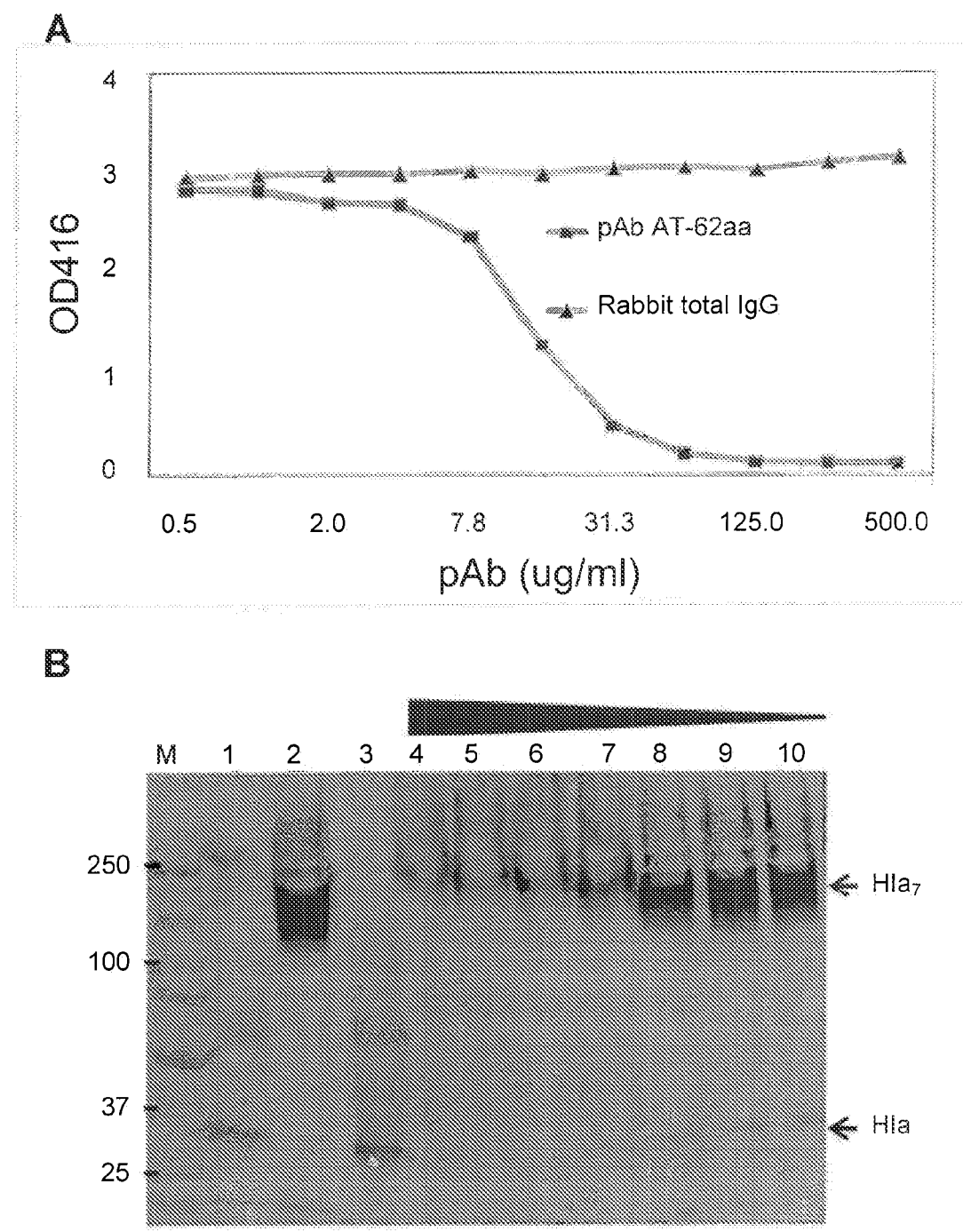
FIGS. 7 (A and B)—(A) Determination of 50% neutralization titer (NT$_{50}$) of rabbit anti-AHL-62aa polyclonal antibody (pAb) against 1 μg/ml Hla. (B) Toxin oligomerization inhibition with anti-Hla-62aa pAb. Rabbit RBCs were incubated with Hla alone or Hla pre-incubated with pAb. Lane 1: boiled; lane 2 at 4° C., lane 3: Hla control without RBC; lanes 4-10: 15 μg/ml of Hla neutralized with decreasing concentration of anti-Hla-62aa pAb (AT-62aa) (two fold diluted from 400 to 6.25 μg/ml).

To examine the mechanism of neutralization, the effect of AHL-62aa pAb on heptameric oligomer (Hla7) formation was tested in a Western blot assay. Hla was incubated with pAbs before incubating the mixture with RBCs. The cell lysates were subjected to Western blotting without prior boiling. In particular, the mixtures were incubated with 2% rabbit RBC for 30 min at 37° C. and loaded in SDS-PAGE without heating. The Western blot was developed with sheep anti-Hla polyclonal antibody. FIG. 7B shows that pAbs to AHL-62aa prevented the formation of heptameric (Hla7) structure.

Example 7

Polyclonal Antibodies Against AHL-62aa Protect Mice Against Community-Acquired Methicillin-Resistant Staphylococcus aureus The protective efficacy of AHL-62aa antibodies against community-acquired MRSA human infection causing isolates (CA-MRSA USA300) was evaluated. AHL-62aa specific antibodies obtained from rabbits vaccinated with AHL-62aa vaccine were used as an example of passive protection in a previously described MRSA mouse infection model (Fattom, A. I., et al., A Staphylococcus aureus capsular polysaccharide (CP) vaccine and CP-specific antibodies protect mice against bacterial challenge. Infect Immun, 1996. 64(5): p. 1659-65). The efficacy was tested against CA-MRSA USA300 lethal challenge in Hog-Mucin bacteremia model. Using this model, 9-10 week old female BALM mice in groups of five were intra-peritoneal (IP) administered AHL-62aa-IgG at total polyclonal IgG doses of 5 mg, 2.5 mg, 1.25 mg, 0.625 mg, while mice in control groups were given 5 mg of control IgG (naïve rabbit IgG) or saline-placebo and then IP challenged 24 hours later with 5×10$^4$ CA-MRSA USA300 (LAC) plus 3% hog mucin. The protective efficacy of AHL-62aa-IgG was then evaluated at 7-days of post bacterial challenge survival.

TABLE 4

PROTECTION AGAINST MRSA

| Treatment | Passive Immunization (-24 Hours) Dose (Total Poly-IgG) | CA-MRSA USA300 Challenge (0 Hours) | Survivor/ total | % survival |
|---|---|---|---|---|
| AHL62aa-IgG | 5 mg | 5 × 10$^4$ + 3% mucin | 10/10 [1] | 100% |
| AHL62aa-IgG | 2.5 mg | 5 × 10$^4$ + 3% mucin | 4/5 | 40% |
| AHL62aa-IgG | 1.25 mg | 5 × 10$^4$ + 3% mucin | 2/5 | 20% |
| AHL62aa-IgG | 0.625 mg | 5 × 10$^4$ + 3% mucin | 0/5 | 0% |
| Control IgG | 5 mg | 5 × 10$^4$ + 3% mucin | 1/10 [1] | 10% |
| Placebo | n/a | 5 × 10$^4$ + 3% mucin | 0/5 | 0% |

[1] data include two groups of 5 mice each from two independent experiments.

Table 4 shows an example of dose-dependent efficacy of rabbit polyclonal IgG generated using AHL-62aa vaccine as an immunogen. When passively immunized, 5 mg AHL62aa-IgG conferred 100% protection, 2.5 mg AHL62aa-IgG confers 40% protection, 1.25 mg AHL62aa-IgG confers 20% protection, 0.625 mg AHL62aa-IgG confers 0% protection, versus 10% survival with 5 mg control IgG or 0% with placebo.

Example 8

Antibodies to AHL-62aa Synergize with PVL Antibodies to Protect Mice from Lethal Bacteremia This example shows that antibodies raised against AHL-62aa synergize with antibodies against another pore forming toxin, Panton-valentine leucocidin (PVL). Antibodies were raised against the S subunit of PVL (LukS-PV) in rabbits and anti-LukS IgG was purified. Specific anti-LukS was further purified from this antibody using an affinity column with purified LukS conjugated with synthetic beads. Mice were treated with control IgG, AHL-62aa-IgG, purified anti-LukS, or combination of the antibodies and challenged with 5×10$^4$ CFU of USA300 MRSA strain (LAC). Mice were monitored for 5 days for morbidity and mortality. AHL-62aa IgG showed a synergistic effect when combined with purified anti-LukS antibodies (see Table 5).

TABLE 5

PROTECTION AGAINST BACTEREMIA

| Group | AHL-62aa IgG | Aff. Pur. LukS IgG | Control IgG | S/T | % survival |
|---|---|---|---|---|---|
| 1 | 0 | 0 | 2 mg | 0/5 | 0% |
| 2 | 2 mg | 0 | 0 | 2/5 | 40% |
| 3 | 0 | 50 ug | 2 mg | 3/5 | 60% |
| 4 | 2 mg | 12.5 ug | 0 | 4/5 | 80% |
| 5 | 2 mg | 25 ug | 0 | 5/5 | 100% |
| 6 | 2 mg | 50 ug | 0 | 5/5 | 100% |

S/T: survivor/total

Table 5 shows synergy between antibodies raised against AHL-62aa and LukS-PV in protection against USA300 bacteremia (% survival). These data show that passive immunization with antibodies raised against Hla mutant vaccines can complement and enhance the protective efficacy of other *S. aureus* antigens.

Example 9

Figure 8:
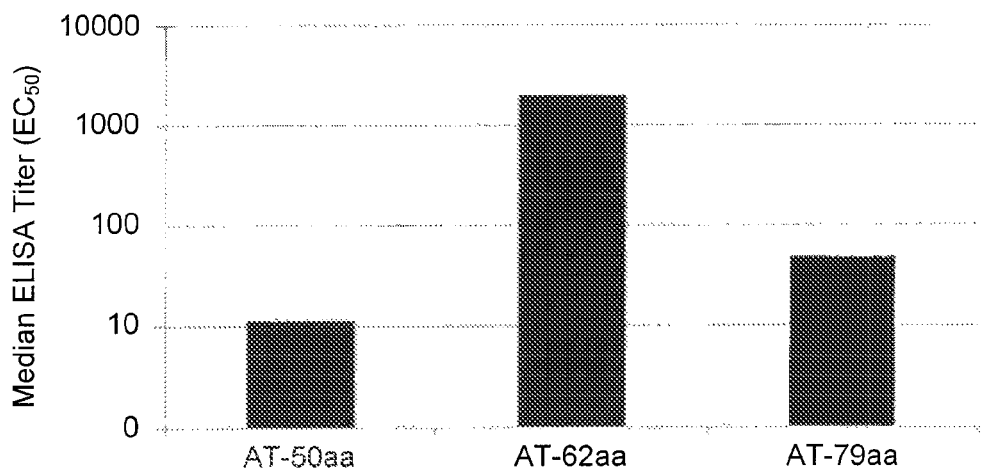
FIGS. 8 (A and B)—(A) Determination of median ELISA titer (EC$_{50}$) of total antibodies to alpha-toxin (Hla) in mouse sera obtained from mice (n=20/group) immunized with 10 μg of met-AHL50-leu-glu-his$_6$ (AT-50aa), met-AHL62-leu-glu-his$_6$ (AT-62aa), or met-AHL79-leu-glu-his$_6$ (AT-79aa), each formulated with IDC-1001 adjuvant. (B) Determination of neutralization titer (NT$_{50}$) of neutralizing antibodies to Hla in mouse sera obtained from mice (n=5/group) immunized with 10 μg of AHL-50aa (AT-50aa), AHL-62aa (AT-62aa), or AHL-79aa (AT-79aa), each formulated with IDC-1001.
Figure 8:
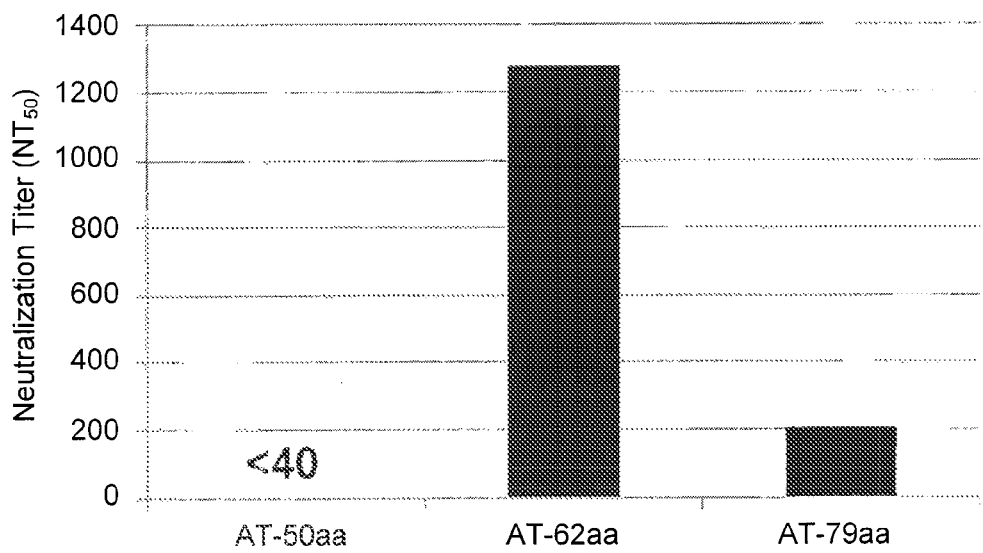

Comparison of Immunogenicity and In Vivo Efficacy of AHL-50aa, AHL-62-aa, and AHL-79aa AHL-50aa protein was previously reported as a vaccine candidate against pneumonia by *S. aureus* Newman strain when used with Freund's adjuvant (Ragle et al. *Infect Immun.* 77: 2712-2718 (2009). Since Freund's adjuvant cannot be used in humans, a comparative efficacy study was performed using met-AHL50-leu-glu-his$_6$ (AHL-50aa), met-AHL62-leu-glu-his$_6$ (AHL-62aa), and met-AHL79-leu-glu-his$_6$ (AHL-79aa) oligopeptides, in combination with IDC-1001 adjuvant, which is currently in clinical development. Groups of 20 mice were immunized IM 3× at two week intervals with 5 µg of AHL-50aa, AHL-62aa or AHL-79aa oligopeptides, or control protein (BSA), each formulated with 5 µg of IDC-1001 in 0.01 ml PBS. On day 35 mice were bled for determination of antibody titers, e.g., for total and neutralizing antibodies to Hla. Antibody titers were determined by ELISA, as described in Examples 4 and 5. Mice immunized with AHL-62aa showed robust ELISA titers with median $EC_{50}$ of 2022 (range: 510-14,900) (FIG. 8A). Mice immunized with AHL-79aa showed lower ELISA titer with median of 49 (range: 0-6,050) followed by mice immunized with AHL-50aa with a median $EC_{50}$ of 11 (range: 0-1,150) (FIG. 8A). Similarly, when neutralization titers were determined in pools of serum samples, mice immunized with AHL-62aa showed highest $NT_{50}$ of 1277 followed by AHL-79aa with $NT_{50}$ of 213 (FIG. 8B). Neutralization was undetectable in the pool of sera from AHL-50aa immunized mice ($NT_{50}$<40) (FIG. 8B).

For the challenge studies each group was broken into two subgroups of 10 mice each and challenged as described below in Examples 10 and 11 to determine vaccine efficacy against *S. aureus* pneumonia and sepsis.

Example 10

Figure 9:
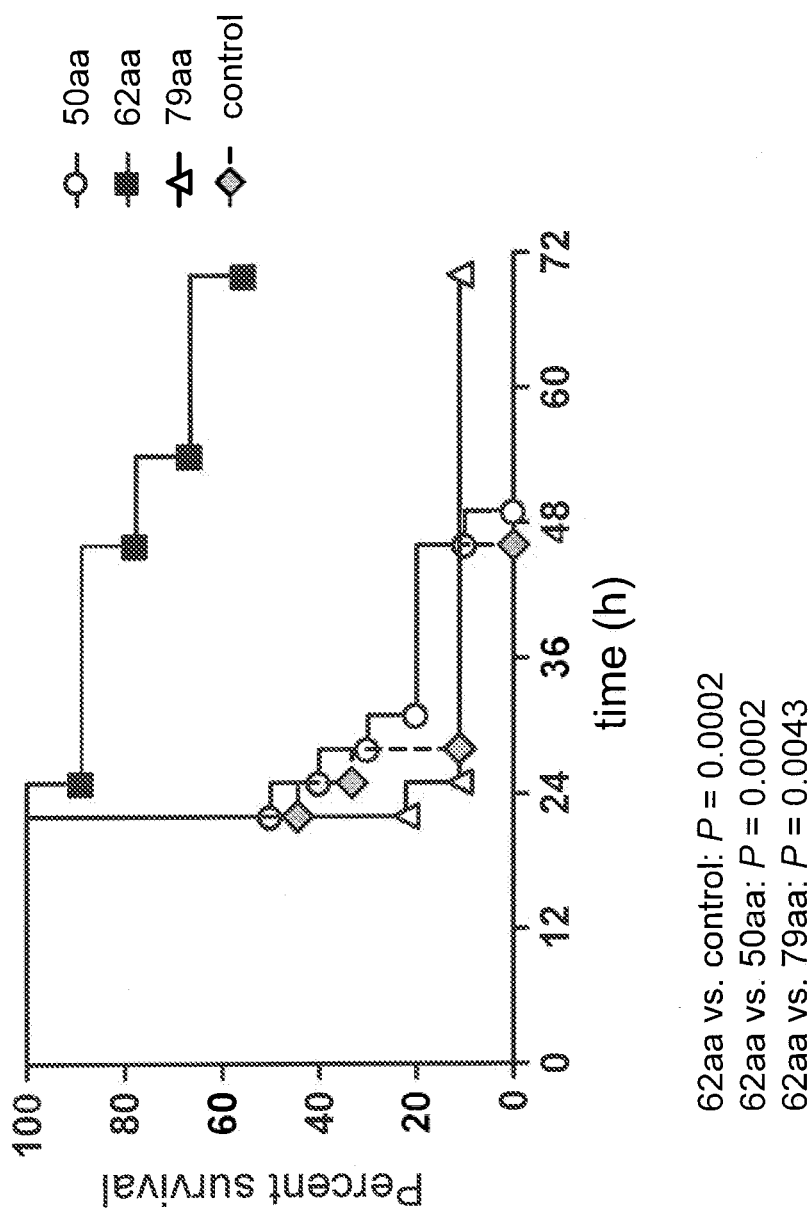
FIG. 9—Percent (%) survival of mice (n=10/group) immunized with 10 μg of met-AHL50-leu-glu-his$_6$ (50aa), met-AHL62-leu-glu-his$_6$ (62aa), met-AHL79-leu-glu-his$_6$ (79aa), or mice (n=5/group) immunized with control protein (BSA), each in IDC-1001 adjuvant, after IN challenge with 6×10$^7$ CFU of SA Newman strain (62aa vs. control: P=0.0002; 62aa vs. 50aa: P=0.0002; and 62aa vs. 79aa: P=0.0043 using Log-Rank (Mantel-Cox Test)).

Evaluation of In Vivo Efficacy of AHL-62aa and AHL-79aa in a *S. aureus* (Newman Strain) Pneumonia Animal Model Groups of 10 immunized or 5 control mice as described in Example 8, were challenged on day 48 by intranasal (IN) administration of 6×10$^7$ CFU of *S. aureus* (SA) Newman strain. Mice were observed for signs of mortality and morbidity for 7 days. As shown in FIG. 9, mice immunized with control protein or AHL-50aa died within 24-48 hours. Similarly, 9 out of 10 mice immunized with AHL-79aa succumbed to infection, while one mouse survived the challenge. In contrast, mice immunized with AHL-62aa showed 50% protection from lethal challenge with death occurring significantly later than the other groups. No additional lethality was observed in this group beyond 72 hours when the mice were monitored for 7 days.

Example 11

Figure 10:
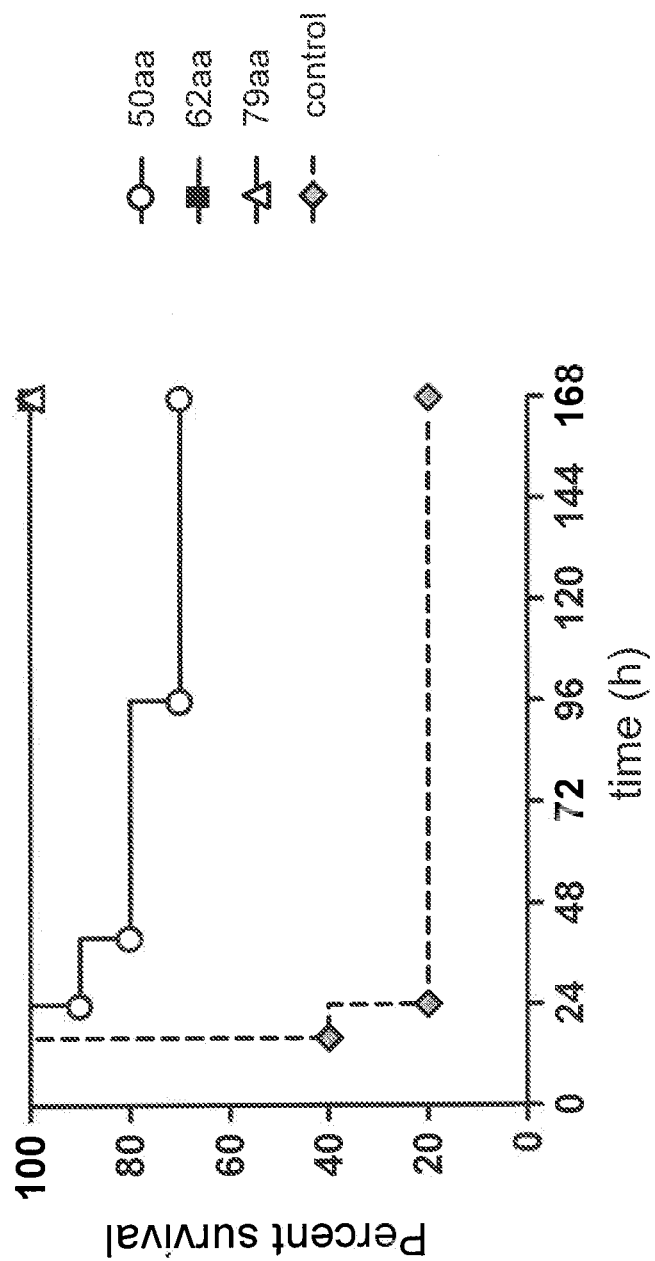
FIG. 10—Percent (%) survival of mice (n=10/group) immunized with 10 μg of met-AHL50-leu-glu-his$_6$ (50aa), met-AHL62-leu-glu-his$_6$ (62aa), met-AHL79-leu-glu-his$_6$ (79aa), or mice (n=5/group) immunized with control protein (BSA), each in IDC-1001 adjuvant, after IP challenge with 5×10$^4$ CFU of SA USA300 strain (LAC) in 3% hog mucin (50aa vs. control: P=0.0147; 62aa/79aa vs. control: P=0.0008; and 62aa/79aa vs. 50aa: P=0.067 using Log-Rank (Mantel-Cox Test)).

Evaluation of In Vivo Efficacy of AHL-62aa and AHL-79aa in a *S. aureus* (US300 Strain) Bacteremia Animal Model Groups of 10 immunized or 5 control mice as described in Example 8, were challenged on day 41 by intraperitoneal (IP) administration of 5×10$^4$ CFU of SA USA300 (LAC), in 3% hog mucin. Mice were observed for signs of mortality and morbidity for 7 days. As shown in FIG. 10, mice immunized with AHL-62aa or AHL-79aa survived the challenge while 30% of mice immunized with AHL-50aa and 80% of control mice died from the infection.

Example 12

Figure 11:
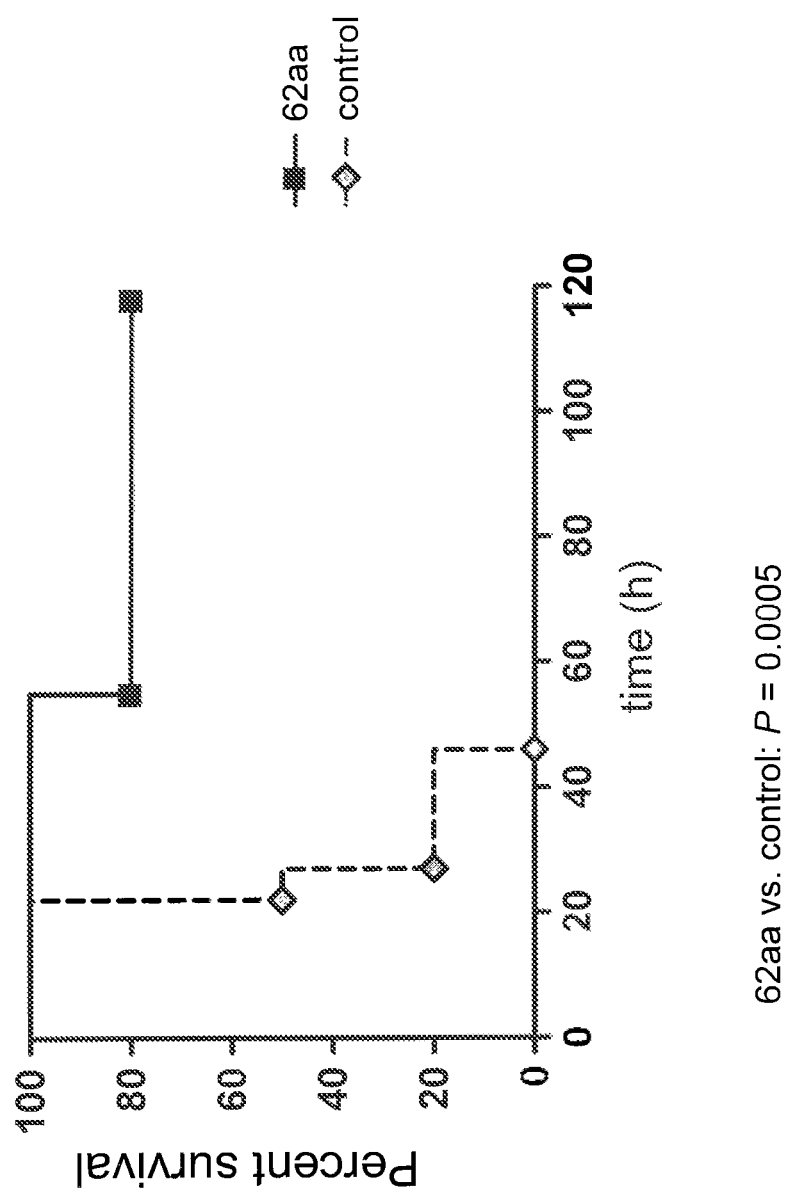
FIG. 11—Percent (%) survival of mice (n=5/group) immunized with 10 μg of met-AHL62-leu-glu-his$_6$ (62aa), in IDC-1001 adjuvant, or mice (n=10/group) immunized with IDC-1001 alone, after IN challenge with 1.5×10$^8$ CFU of SA USA300 strain (62aa vs. control: P=0.0005 using Log-Rank (Mantel-Cox Test)).

Evaluation of In Vivo Efficacy of AHL-62aa in a *S. aureus* (US300 Strain) Pneumonia Animal Model The efficacy of AHL-62aa was further explored against pneumonia induced by SA USA300 (LAC). Groups of 5 female six week old BALB/c mice, were immunized IM 3× at two week intervals with 10 µg of AHL-62aa formulated with 20 µg of IDC-1001 in 0.01 ml PBS, and groups of 10 "control" mice were immunized with IDC-1001 alone in 0.01 ml PBS. On days 21 and 35 mice were bled for determination of antibody titers, e.g., total antibodies to Hla. Total antibody titers were determined by ELISA, as described in Example 4. On day 41, mice were challenged by IN administration of 1.5×10$^8$ CFU of SA USA300. On day 35, the immunized mice showed a median antibody titer ($EC_{50}$) of 3640 with a range of 2400 to 8980 on ELISA plated coated with wild type Hla. Control mice showed no detectable antibody titers. As shown in FIG. 11, while all control mice died within 20-48 hours, 4 out of 5 immunized mice survived the challenge, indicating the efficacy of AHL-62aa against SA USA300 induced pneumonia.

Example 13

Passive Immunization with Antibodies Against AHL-62aa Reduce Bacterial Load in Organs of *S. aureus* Infected Mice This example evaluates the protective in vivo efficacy of AHL-62aa antibodies in inhibiting bacterial dissemination and/or growth. Two studies were performed using the pneumonia and bacteremia models. Polyclonal AHL-62aa specific antibodies (anti-AHL-62aaIgG) were raised against purified AHL-62aa in rabbits and anti-AHL-62aa IgG was purified by Protein A. Control naïve rabbit IgG was acquired from a commercial source (EQUITECH-BIO, Inc.).

Figure 12:
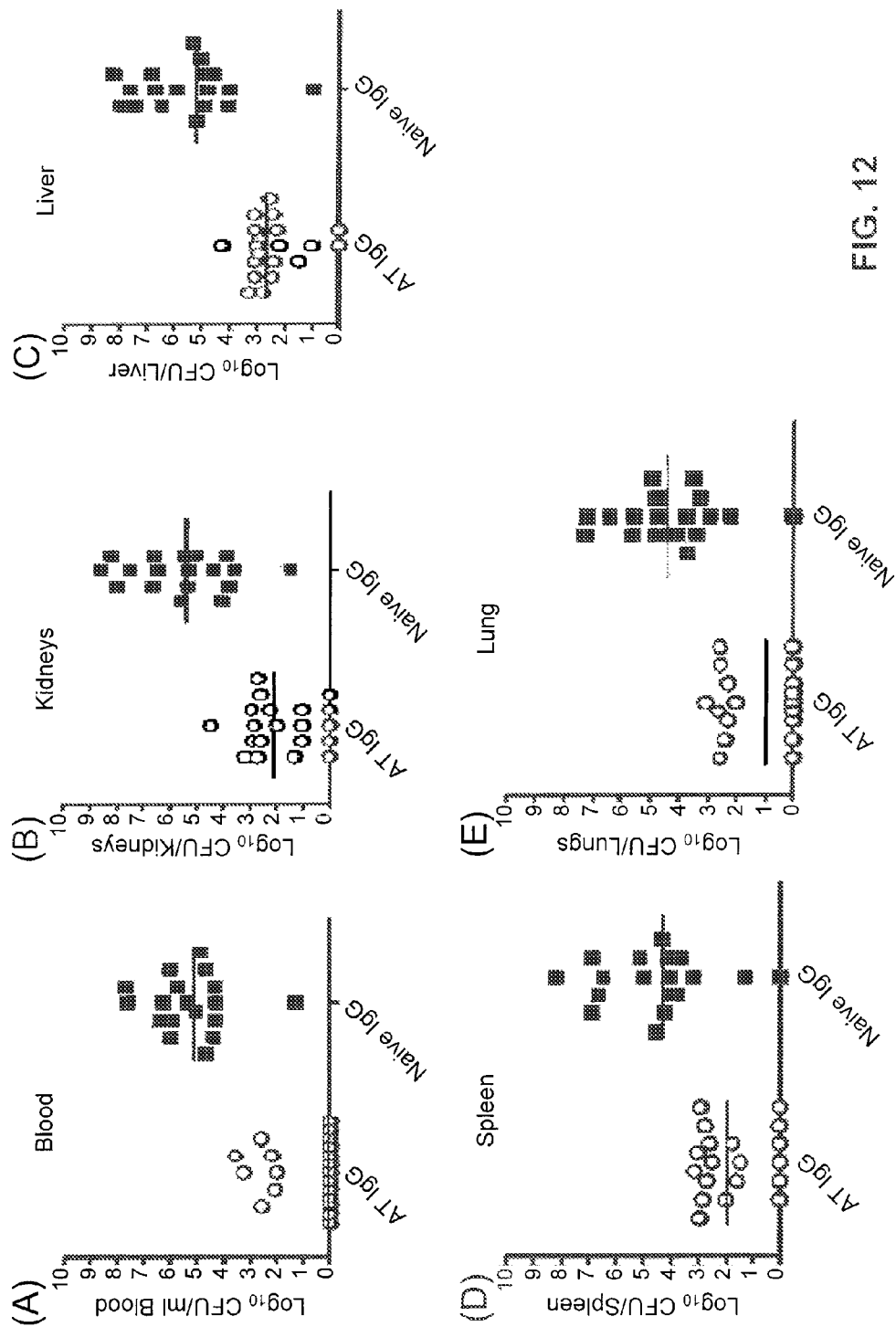
FIG. 12 (A-E)—Bacterial burden in (A) blood ($\log_{10}$ CFU/ml blood), (B) kidneys ($\log_{10}$ CFU/kidneys), (C) liver ($\log_{10}$ CFU/liver), (D) spleen ($\log_{10}$ CFU/spleen), and (E) lung ($\log_{10}$ CFU/lung) after passive immunization of mice (n=20/group) with anti-AHL-62aa IgG (AT IgG) or naïve IgG, followed by IP challenge with 5×10$^4$ CFU of SA USA300 strain in 3% hog mucin. Samples with no bacterial growth were empirically given a $\log_{10}$ value of "0". (AT IgG vs. naïve IgG: P<0.0001 in all cases using Mann Whitney Test).

In the first experiment two groups of 20 mice were passively immunized, one group with naïve IgG and the other group with anti-AHL-62aa IgG. After 24 hours mice were infected IP (bacteremia model) with 5×10$^4$ CFU of SA USA300 in 3% hog mucin. 12 hours after infection mice were euthanized and blood and various organs were aseptically removed and prepared as follows: each organ was homogenized with 3.2 mm stainless steel beads using a Bullet Blender (Next Advance Inc.) and were taken up in a total volume of 500 ul PBS. Serial dilutions of blood and organ homogenates were prepared in PBS and streaked out onto BHI agar plates. After an overnight incubation at 37° C. CFU counts on the plates were manually enumerated. In this experiment, 2 of the control mice died before the 12 hour time point, thus data could be collected only from 18 control mice. All 20 mice in the AHL-62aa IgG treated group were alive at the time of sacrifice. As shown in FIG. 12 (A-E), treatment with anti-AHL-62aa IgG resulted in drastic reduction of bacterial burden in blood (FIG. 12A), kidney (FIG. 12B), liver (FIG. 12C), spleen (FIG. 12D), and lung (FIG. 12E). The results show antibodies against AHL-62aa were protective against dissemination of bacteria in vivo.

Figure 13:
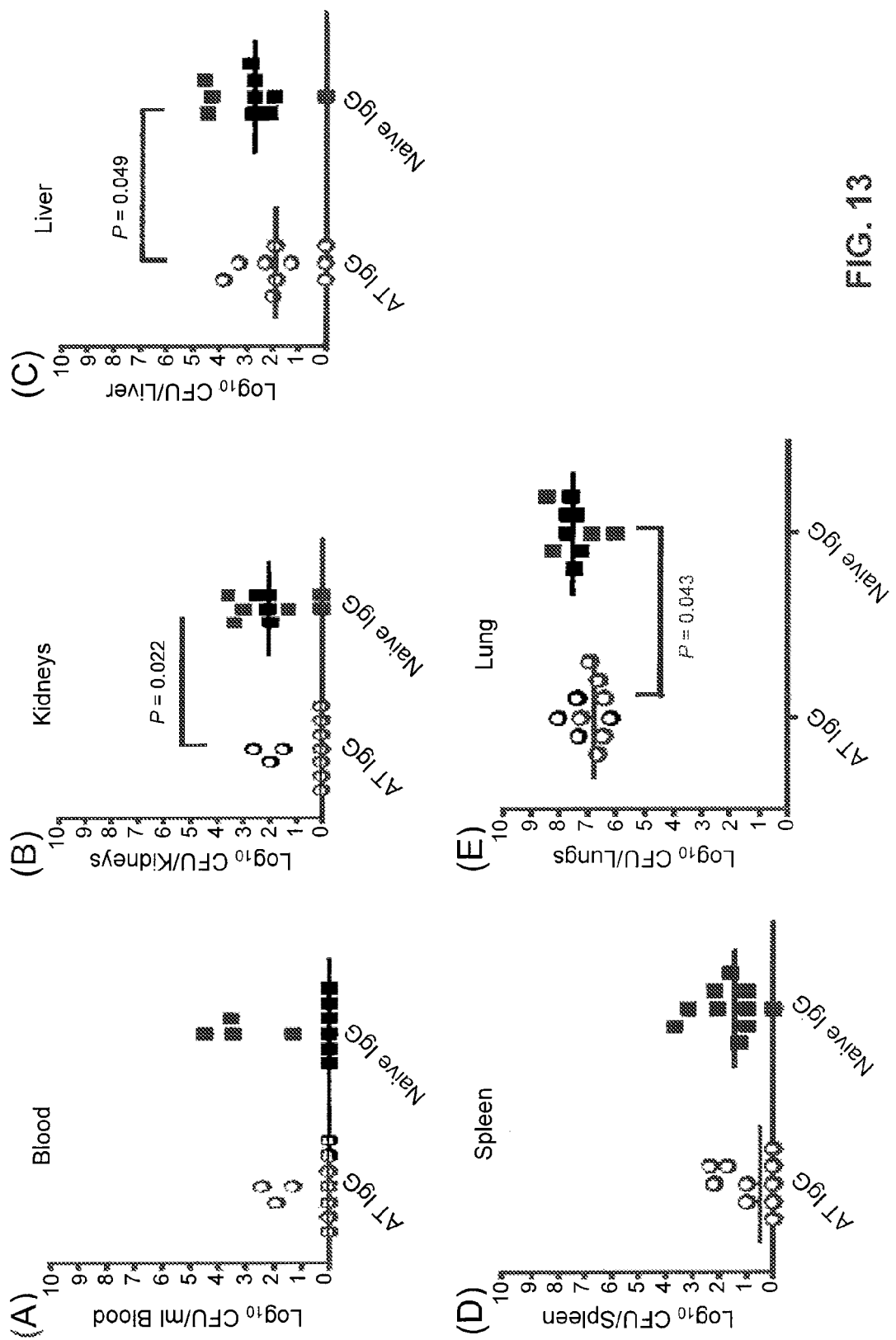
FIG. 13 (A-E)—Bacterial burden in (A) blood ($\log_{10}$ CFU/ml blood), (B) kidneys ($\log_{10}$ CFU/kidneys), (C) liver ($\log_{10}$ CFU/liver), (D) spleen ($\log_{10}$ CFU/spleen), and (E) lung ($\log_{10}$ CFU/lung) after passive immunization of mice (n=20/group) with anti-AHL-62aa IgG (AT IgG) or naïve IgG, followed by IN challenge with 1.3×10$^8$ CFU of SA USA300 strain. Samples with no bacterial growth were empirically given a $\log_{10}$ value of "0". (AT IgG vs. naïve IgG: P=0.022 for kidneys, P=0.049 for liver, and P=0.043 for lung using Maim Whitney Test).

In the second experiment, two groups of 10 mice were passively immunized, one group with naïve IgG and the other group with anti-AHL-62aa IgG. After 24 hours mice were infected IN (pneumonia model) with $1.3 \times 10^8$ CFU of SA USA300. 12 hours after infection mice were euthanized and blood and various organs were aseptically removed and prepared as described above. CFUs were determined in blood and organ homogenates as described above. As shown in FIG. 13 (A-E), treatment with AHL-62aa IgG resulted in reduction of bacterial burden in blood (FIG. 12A), kidney (FIG. 12B), liver (FIG. 12C), spleen (FIG. 12D), and lung (FIG. 12D). Statistical analysis using Mann Whitney test showed that the differences were significant for kidneys, liver and lung. A trend could also be observed in blood and spleen. Five out of 10 mice treated with anti-AHL-62aa IgG showed no bacterial seeding in spleen, while 9 out of 10 mice had infected spleens.

These data show that antibodies induced by AHL-62aa were protective against dissemination of bacteria in vivo.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated fusion oligopeptide at least 70 amino acids in length but no more than 100 amino acids in length, comprising a first amino acid sequence fused to a second amino acid sequence, wherein the first amino acid sequence is at least 95% identical to amino acids 27-88 of SEQ ID NO:2.

2. The oligopeptide of claim 1, comprising amino acids 27-88 of SEQ ID NO:2.

3. The oligopeptide of claim 1, wherein the second amino acid sequence is identical to amino acids 249-262 of SEQ ID NO:2, or identical except for up to three single amino acid substitutions, insertions, or deletions.

4. The oligopeptide of claim 3, wherein the second amino acid sequence is identical to amino acids 249-262 of SEQ ID NO:2.

5. The oligopeptide of claim 3, further comprising a linker between the first amino acid sequence and the second amino acid sequence.

6. The oligopeptide of claim 3, wherein the linker comprises at least one, but no more than 15 amino acids selected from the group consisting of glycine, serine, alanine, or a combination thereof.

7. A polypeptide comprising the oligopeptide of claim 1, and further comprising a heterologous amino acid sequence.

8. An isolated polynucleotide comprising a nucleic acid which encodes the oligopeptide of claim 1.

9. A vector comprising the polynucleotide of claim 8.

10. A host cell comprising the vector of claim 9.

11. A method of producing an alpha-hemolysin oligopeptide, comprising culturing the host cell of claim 10, and recovering the oligopeptide.

12. A composition comprising the oligopeptide of claim 1 and a carrier.

13. The composition of claim 12, further comprising an adjuvant.

14. The composition of claim 13, further comprising an immunogen.

15. A method of producing a vaccine against *S. aureus* infection comprising:
 (a) isolating the oligopeptide of claim 1; and
 (b) combining the oligopeptide with an adjuvant.

16. The oligopeptide of claim 1, wherein the second amino acid sequence is an additional fragment of SEQ ID NO:2.

17. The polypeptide of claim 7, wherein the heterologous amino acid sequence is an N-terminal signal or leader sequence, a linker sequence, an immunoglobulin Fc region, a T-cell epitope, a B-cell epitope, a cytokine, a chemokine, or albumin.

18. The polypeptide of claim 7, wherein the heterologous amino acid sequence is: an immunogenic polypeptide or epitope from *Staphylococcus*; an immunogenic polypeptide or epitope from another bacterium; or an immunogenic polypeptide or epitope from a virus.

* * * * *

SEQUENCE LISTING

<160> NUMBER OF SEQ ID NOS: 8

<210> SEQ ID NO 1
<211> LENGTH: 960
<212> TYPE: DNA
<213> ORGANISM: Staphylococcus aureus

<400> SEQUENCE: 1

```
atgaaaacac gtatagtcag ctcagtaaca acaacactat tgctaggttc catattaatg      60
aatcctgtcg ctaatgccgc agattctgat attaatatta aaaccggtac tacagatatt     120
ggaagcaata ctacagtaaa aacaggtgat ttagtcactt atgataaaga aaatggcatg     180
cacaaaaaag tattttatag ttttatcgat gataaaaatc ataataaaaa actgctagtt     240
attagaacga aaggtaccat tgctggtcaa tatagagttt atagcgaaga aggtgctaac     300
aaaagtggtt tagcctggcc ttcagccttt aaggtacagt tgcaactacc tgataatgaa     360
gtagctcaaa tatctgatta ctatccaaga aattcgattg atacaaaaga gtatatgagt     420
actttaactt atggattcaa cggtaatgtt actggtgatg atacaggaaa aattggcggc     480
cttattggtg caaatgtttc gattggtcat acactgaaat atgttcaacc tgatttcaaa     540
acaattttag agagcccaac tgataaaaaa gtaggctgga aagtgatatt taacaatatg     600
gtgaatcaaa attggggacc atatgataga gattcttgga acccggtata tggcaatcaa     660
cttttcatga aaactagaaa tggctctatg aaagcagcag ataacttcct tgatcctaac     720
aaagcaagtt ctctattatc ttcagggttt tcaccagact tcgctacagt tattactatg     780
gatagaaaag catccaaaca acaaacaaat atagatgtaa tatacgaacg agttcgtgat     840
gactaccaat tgcactggac ttcaacaaat tggaaaggta ccaatactaa agataaatgg     900
atagatcgtt cttcagaaag atataaaatc gattgggaaa aagaagaaat gacaaattaa     960
```

<210> SEQ ID NO 2
<211> LENGTH: 319
<212> TYPE: PRT
<213> ORGANISM: Staphylococcus aureus

<400> SEQUENCE: 2

```
Met Lys Thr Arg Ile Val Ser Ser Val Thr Thr Leu Leu Leu Gly
1               5                   10                  15

Ser Ile Leu Met Asn Pro Val Ala Asn Ala Ala Asp Ser Asp Ile Asn
            20                  25                  30

Ile Lys Thr Gly Thr Thr Asp Ile Gly Ser Asn Thr Thr Val Lys Thr
```

```
                35                  40                  45
Gly Asp Leu Val Thr Tyr Asp Lys Glu Asn Gly Met His Lys Lys Val
 50                  55                  60

Phe Tyr Ser Phe Ile Asp Asp Lys Asn His Asn Lys Lys Leu Leu Val
 65                  70                  75                  80

Ile Arg Thr Lys Gly Thr Ile Ala Gly Gln Tyr Arg Val Tyr Ser Glu
                 85                  90                  95

Glu Gly Ala Asn Lys Ser Gly Leu Ala Trp Pro Ser Ala Phe Lys Val
                100                 105                 110

Gln Leu Gln Leu Pro Asp Asn Glu Val Ala Gln Ile Ser Asp Tyr Tyr
            115                 120                 125

Pro Arg Asn Ser Ile Asp Thr Lys Glu Tyr Met Ser Thr Leu Thr Tyr
        130                 135                 140

Gly Phe Asn Gly Asn Val Thr Gly Asp Thr Gly Lys Ile Gly Ile Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Ile Asp Arg Ser
    290                 295                 300

Ser Glu Arg Tyr Lys Ile Asp Trp Glu Lys Glu Met Thr Asn
305                 310                 315

<210> SEQ ID NO 3
<211> LENGTH: 219
<212> TYPE: DNA
<213> ORGANISM: Artificial Sequence
<220> FEATURE:
<223> OTHER INFORMATION: met-AHL62-leu-glu-his6

<400> SEQUENCE: 3
catatggcag attctgatat taatattaaa accggtacta cagatattgg aagcaatact      60
acagtaaaaa caggtgattt agtcacttat gataaagaaa atggcatgca caaaaaagta    120
ttttatagtt ttatcgatga taaaaatcat aataaaaaac tgctagttat tagaacgaaa    180
ggtaccattg ctctcgagca ccaccaccac caccactga                            219

<210> SEQ ID NO 4
<211> LENGTH: 71
<212> TYPE: PRT
<213> ORGANISM: Artificial Sequence
<220> FEATURE:
<223> OTHER INFORMATION: met-AHL62-leu-glu-his6
```

<400> SEQUENCE: 4

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
                20                  25                  30

Asn Gly Met His Lys Lys Val Phe Tyr Ser Phe Ile Asp Asp Lys Asn
            35                  40                  45

His Asn Lys Lys Leu Leu Val Ile Arg Thr Lys Gly Thr Ile Ala Leu
        50                  55                  60

Glu His His His His His His
65                  70

<210> SEQ ID NO 5
<211> LENGTH: 270
<212> TYPE: DNA
<213> ORGANISM: Artificial Sequence
<220> FEATURE:
<223> OTHER INFORMATION: met-AHL79-leu-glu-his6

<400> SEQUENCE: 5
catatggcag attctgatat taatattaaa accggtacta cagatattgg aagcaatact      60
acagtaaaaa caggtgattt agtcacttat gataaagaaa atggcatgca caaaaaagta     120
ttttatagtt ttatcgatga taaaaatcat aataaaaaac tgctagttat tagaacgaaa     180
ggtaccattg ctgggggcgg agggttttca ccagacttcg ctacagttat tactatggat     240
agactcgagc accaccacca ccaccactga                                      270

<210> SEQ ID NO 6
<211> LENGTH: 88
<212> TYPE: PRT
<213> ORGANISM: Artificial Sequence
<220> FEATURE:
<223> OTHER INFORMATION: met-AHL79-leu-glu-his6

<400> SEQUENCE: 6

Met Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
                20                  25                  30

Asn Gly Met His Lys Lys Val Phe Tyr Ser Phe Ile Asp Asp Lys Asn
            35                  40                  45

His Asn Lys Lys Leu Leu Val Ile Arg Thr Lys Gly Thr Ile Ala Gly
        50                  55                  60

Gly Gly Gly Phe Ser Pro Asp Phe Ala Thr Val Ile Thr Met Asp Arg
65                  70                  75                  80

Leu Glu His His His His His His
                85

<210> SEQ ID NO 7
<211> LENGTH: 35
<212> TYPE: DNA
<213> ORGANISM: Artificial Sequence
<220> FEATURE:
<223> OTHER INFORMATION: Forward Primer

<400> SEQUENCE: 7
ttcatatggc agattctgat attaatatta aaacc                                35

<210> SEQ ID NO 8

```
<211> LENGTH: 37
<212> TYPE: DNA
<213> ORGANISM: Artificial Sequence
<220> FEATURE:
<223> OTHER INFORMATION: Reverse Primer

<400> SEQUENCE: 8
ttctcgagtt tattatgatt tttatcatcg ataaaac                                    37
```